United States Patent [19]

Strul

[11] Patent Number: 5,573,533
[45] Date of Patent: Nov. 12, 1996

[54] METHOD AND SYSTEM FOR RADIOFREQUENCY ABLATION OF CARDIAC TISSUE

[75] Inventor: Bruno Strul, Palo Alto, Calif.

[73] Assignee: Medtronic CardioRhythm, San Jose, Calif.

[21] Appl. No.: 866,683

[22] Filed: Apr. 10, 1992

[51] Int. Cl.$^6$ .................................................. A61B 17/39
[52] U.S. Cl. ................................ 606/34; 606/31; 606/42; 606/45; 607/101; 607/102
[58] Field of Search ........................... 606/27–34, 37–42, 606/45–50; 128/784–786, 642

[56] References Cited

U.S. PATENT DOCUMENTS

| | | | |
|---|---|---|---|
| 1,935,289 | 11/1933 | Evans . | |
| 3,588,710 | 6/1971 | Masters . | |
| 3,601,126 | 8/1971 | Estes | 128/783 |
| 3,785,383 | 1/1974 | Dotto | 128/804 |
| 3,800,802 | 4/1974 | Berry et al. | 128/804 |
| 4,204,549 | 5/1980 | Paglione | 128/784 |
| 4,352,156 | 9/1982 | Gyugyi . | |
| 4,494,539 | 1/1985 | Zenitani | 606/33 |
| 4,599,553 | 7/1986 | Brennen et al. . | |
| 4,632,127 | 12/1986 | Sterzer | 128/804 |
| 4,641,649 | 2/1987 | Walinsky et al. . | |
| 4,658,819 | 4/1987 | Harris et al. . | |
| 4,692,685 | 9/1987 | Blaze . | |
| 4,716,897 | 1/1988 | Noguchi et al. | 606/37 |
| 4,727,874 | 3/1988 | Bowers et al. | 606/37 |
| 4,739,759 | 4/1988 | Rexroth et al. | 606/37 |
| 4,805,621 | 2/1989 | Heinze et al. . | |
| 4,862,889 | 9/1989 | Feucht . | |
| 4,878,493 | 11/1989 | Pasternak et al. . | |
| 4,907,589 | 3/1990 | Cosman | 128/784 |
| 4,940,064 | 7/1990 | Desai . | |
| 4,945,912 | 8/1990 | Langberg . | |
| 4,960,134 | 10/1990 | Webster, Jr. . | |
| 4,966,597 | 10/1990 | Cosman . | |
| 5,122,137 | 6/1992 | Lennox | 606/40 |

FOREIGN PATENT DOCUMENTS

| | | |
|---|---|---|
| 0136855 | 4/1985 | European Pat. Off. . |
| 0368532 | 5/1990 | European Pat. Off. . |
| 62-120861 | 6/1987 | Japan . |
| 2164473 | 3/1986 | United Kingdom . |
| WO91/03208 | 3/1991 | WIPO . |
| WO91/16859 | 11/1991 | WIPO . |
| WO93/08757 | 5/1993 | WIPO . |
| WO93/08756 | 5/1993 | WIPO . |

OTHER PUBLICATIONS

Kuck et al. (1991) Lancet 337:1557–1561.
Langberg et al. (1991) Am. J. Cardiol. 67:142–147.
Kuck et al. (1991) Circulation 84:2366–2375.
Hat 200 S Brochure, Dr. Ing. P. Osypka GmbH, 6 pp.
Cerablate® Brochure, Dr. Ing. P. Osypka GmbH, 1 page.
Fackelmann (1991) Science News 140:42–43.
Haverkamp, W. et al. "Radiofrequency current catheter coagulation using pulsed energy delivery," Zeitschrift fur Kardiologie Z Kardiol 81:140–144 (1992).

*Primary Examiner*—Angela D. Sykes
*Assistant Examiner*—Michael Peffley
*Attorney, Agent, or Firm*—Townsend and Townsend Khourie and Crew

[57] ABSTRACT

A system for delivering radiofrequency energy to ablate cardiac tissue comprises a radiofrequency generator and an intravascular catheter. The catheter includes both a radiofrequency ablation electrode and a temperature sensor within its distal end. Delivery of power to the ablation electrode may then be controlled based on electrode temperature using a cascade control system wherein analog temperature controller adjusts the set point to a secondary power controller. Alternatively, power delivered to the patient can be controlled directly based on a power set point. Reuse of the catheter is prevented by a fuse within the catheter which is sensed prior to power delivery and broken prior to disconnection of the catheter.

17 Claims, 29 Drawing Sheets

| FIG. 7A. | FIG. 7B. | FIG. 7C. |
| --- | --- | --- |
| FIG. 7D. | FIG. 7E. | FIG. 7F. |

| FIG. 8A. | FIG. 8B. |
| --- | --- |
| FIG. 8C. | FIG. 8D. |

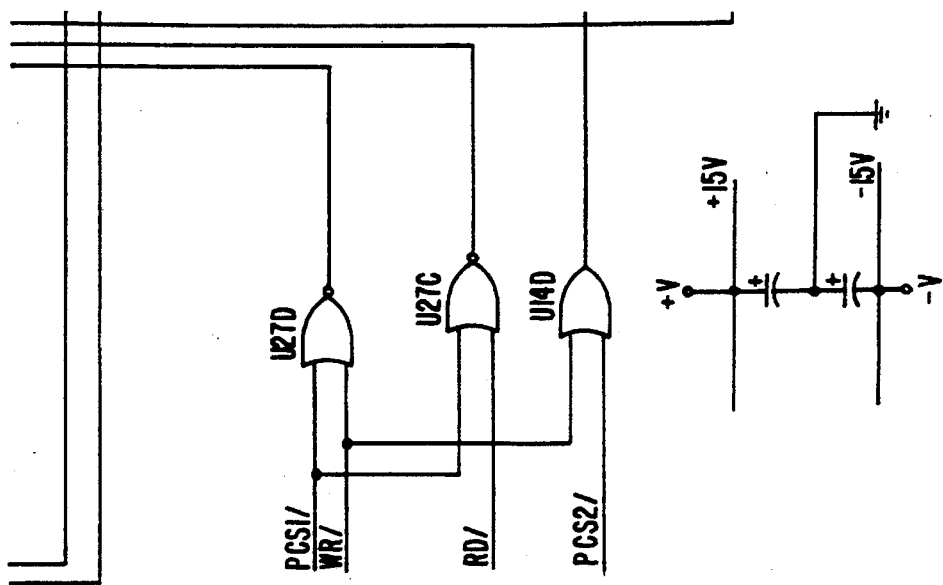
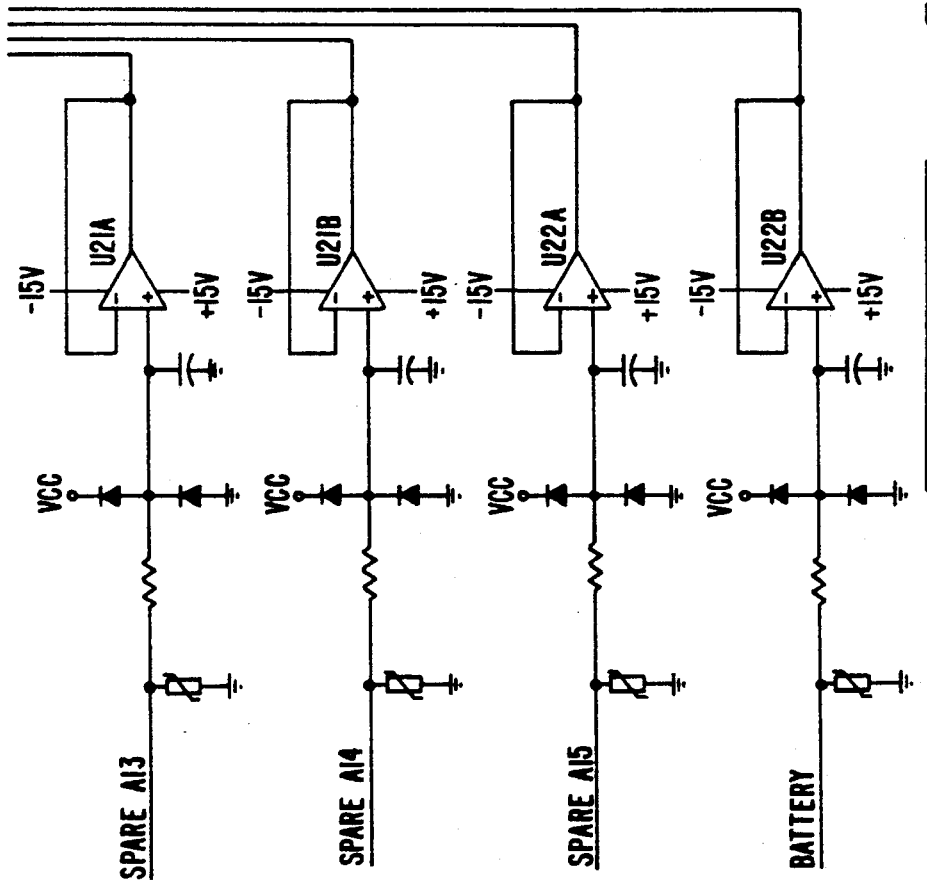
FIG. 9C.
FIG. 9.
| FIG. 9A. | FIG. 9B. |
| --- | --- |
| FIG. 9C. | FIG. 9D. |

METHOD AND SYSTEM FOR RADIOFREQUENCY ABLATION OF CARDIAC TISSUE

BACKGROUND OF THE INVENTION

1. Field of the Invention

The present invention relates generally to the field of electrophysiology. More particularly, this invention relates to methods and apparatus for treating cardiac arrhythmias.

Symptoms of abnormal heart rhythm are generally referred to as cardiac arrhythmias, with an abnormally slow rhythm being classified as a bradycardia and an abnormally rapid rhythm being referred to a tachycardia. The present invention is concerned with the treatment of tachycardias which are frequently caused by the presence of an "arrhythmogenic site" or "accessory atrioventricular pathway" close to the inner surface of one of the chambers of the heart. The heart includes a number of normal pathways which are responsible for the propagation of signals necessary for the normal electrical function. The presence of arrhythmogenic sites or accessory pathways can bypass or short circuit the normal pathways, potentially resulting in very rapid heart contractions, referred to as tachycardias. Tachycardias may be defined as ventricular tachycardias (VT's) and supraventricular tachycardias (SVT's). VT's originate in the left or right ventricle and are typically caused by arrhythmogenic sites associated with a prior myocardial infarction. SVTt's originate in the atria and are typically caused by an accessory pathway.

Treatment of beth ventricular and supraventricular tachycardias may be accomplished by a variety of approaches, including drugs, surgery, implantable pacemakers/defibrillators, and catheter ablation. While drugs may be the treatment of choice for many patients, they only mask the symptoms and do not cure the underlying cause. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. The catheter-based treatments rely on the application of various destructive energy sources to the target tissue, including direct current electrical energy, radiofrequency electrical energy, laser energy, and the like.

Of particular interest to the present invention are radiofrequency ablation protocols which have proven to be highly effective in tachycardia treatment while exposing the patient to minimum side effects and risks.

Radiofrequency catheter ablation is generally performed after an initial mapping procedure where the location of the arrhythmogenic sites and accessory pathways are determined. After mapping, a catheter having a suitable electrode is introduced to the appropriate chamber and manipulated so that the electrode lies proximate the accessory pathway. Radiofrequency energy is then applied through the electrode to the cardiac tissue in order to ablate a region of the tissue which forms part of the accessory pathway. By successfully destroying that tissue, the accessory pathway or arrhythmogenic site is destroyed so that the abnormal signalling patterns responsible for the tachycardia will no longer occur.

While very promising, radiofrequency ablation suffers from certain disadvantages. The application of radiofrequency energy to the heart tissue can have complications, particularly if the directed energy has not been properly controlled. Many systems which have been used thus far for radiofrequency ablation have utilized radiofrequency power supplies originally intended for electrosurgery and electrocautery. While such power supplies are workable, they do not provide power control of a type which is best used with cardiac tissue ablation and can subject the patient to spurious ground potentials. Such ground potentials can be a problem when the heart is being treated. Such conventional radiofrequency power supplies are also usually bulky and relatively heavy because of the need to provide power supply transformers.

2. Description of the Background Art

The successful treatment of supraventricular and ventricular tachycardias by radiofrequency catheter ablation of accessory atrioventricular pathways is described in Kuck et al. (1991) Lancet 337:1557–61; Langberg et al. (1991) Am. J. Cardiol. 67:142–47; and Kuck et al. (1991) Circulation 84:2366–2375. Catheters useful for the intracardiac application of radiofrequency energy are described in U.S. Pat. Nos. 4,945,912; 4,940,064; and 4,641,649. A power supply and radiofrequency ablation catheter suitable for intracardiac tissue ablation are available from Dr. Osypka GMBH under the tradenames HAT 200 S and CERABLATE®, respectively. The power supply and catheter together permit ablation to be performed under a digital temperature control mode. The present state of cardiac radiofrequency ablation treatment is summarized in Fackelmann (1991) Science News 140:42–43.

SUMMARY OF THE INVENTION

An improved method for radiofrequency ablation of cardiac tissue relies on the introduction of an electrode to a target site, typically the location of an accessory pathway, within an interior chamber of a patient's heart. Radiofrequency energy is applied to the target location through the electrode from an external power source, where the amount of radiofrequency energy delivered is controlled based on a particular temperature control protocol which has been found to provide very precise control of the ablation temperature. Such precise temperature control reduces the risk of unintended damage to the cardiac tissue and, in particular, provides for better localization of the treatment. That is, tissue necrosis is more accurately limited to within the target region than with non-temperature controlled protocols. The temperature control protocol also limits the total amount of energy delivered to achieve the desired tissue ablation by reducing the duty cycle of the power source. The reduced duty cycle is of particular advantage in that a more controlled ablation result is obtained. The use of a battery power source is advantageous since it reduces or eliminates the generation of spurious ground differential currents, which can be a particular problem in equipment used with the heart.

The temperature control protocol comprises measuring temperature at the target location, typically using a temperature sensor within the treatment electrode. The resulting actual temperature signal is amplified and then compared with a temperature set point signal, and a power set point signal is produced based on the deviation between the actual temperature and temperature set point. Power output from the power source (typically an output power oscillator connected to a battery) is measured to produce an actual power signal, and the actual power signal is compared with the power set point to produce a power output signal based on the difference between the set point and the actual power. Power from the power source is then controlled based on the power output signal. Usually, both the temperature control and power control loops will be based on proportional control schemes.

In a particular aspect, the present invention provides a method for connecting an intravascular catheter, such as a radiofrequency ablation catheter, to a power source. After connecting a proximal end of the catheter to the power source, the status of a fuse within the catheter is sensed. If the fuse is found to be broken at the time of connection, the power source is disabled, i.e. further use of the catheter is prevented. If the fuse is found to be intact at the time of connection, the fuse will then be broken (typically by passing excess current therethrough) and use of the catheter permitted for so long as it remains connected to the power source. Once the catheter is removed from the power source, the connection method will be repeated to prevent reconnection of used catheter, i.e., those catheters which have been previously connected to the power source and which as a result have broken the internal fuse.

The present invention further provides a radiofrequency power generator which comprises a power source for producing radiofrequency power based on a power output signal. The generator comprises circuitry for measuring the amount of radiofrequency power produced by the power source to produce an actual power signal. An analog temperature controller receives both a temperature set point and an actual temperature signal and, based on the different therebetween, produces a power set point signal. A separate analog power controller receives the power set point signal from the temperature controller and the actual power signal from the power measurement circuitry, and, based on the difference therebetween, produces the power output signal which controls the power source. The generator further comprises an interface for connecting a catheter to the radiofrequency power source and for connecting an external temperature sensor in the catheter to the temperature controller in the generator.

In yet another aspect, the present invention provides a system for radiofrequency ablation of cardiac tissue which comprises both a catheter and a radiofrequency power generator. The catheter includes both an electrode and a temperature sensor near its distal end, and the radiofrequency power generator includes both a power source to deliver radiofrequency power to the electrode and a battery connected to the power source. A temperature controller is further provided for modulating the power to the catheter from the power source. In this way, the total power delivered and power duty cycle can be limited in order to reduce the demand on the battery for the power source.

In a still further embodiment, the present invention provides a radiofrequency ablation system comprising a catheter and a radiofrequency generator connectable to the catheter. A catheter includes electrode near its distal end and a fuse within its body. Circuitry within the generator is capable of sensing the integrity of the fuse when the catheter is initially connected to the generator. Operation of the generator, including the delivery of power to the electrode, is disabled if it is sensed that the fuse is initially broken. Conversely, if it is sensed that the fuse is initially intact, the fuse will be broken by the generator and subsequent operation of the generator, including power delivery to the electrode, will be permitted.

DESCRIPTION OF THE DRAWINGS

FIGS. 7,7a–7f, 8,8a–8d, 9,9a–9d, 10,10a–10d, 11,11a–11c, 12,12a–12c are schematics illustrating the circuitry of the radiofrequency generator of FIG. 4.

DESCRIPTION OF SPECIFIC EMBODIMENTS

The method and apparatus of the present invention are intended for delivering radiofrequency energy to a target location within an interior chamber within a patient's heart, usually the right or left ventricle. The target location will be associated with cardiac tachycardia, usually being an accessory pathway or an arrhythmogenic site responsible for the tachycardia, but also including regions on the bundle of HIS which can non-specifically block tachycardia. Accessory pathways or arrhythmogenic sites responsible for the tachycardia can be identified by conventional intracardiac mapping, as is now amply described in the medical and patent literature. See, for example, U.S. Pat. Nos. 4,699,147; 4,628, 937; and 4,660,571, the disclosures of which are incorporated herein by reference. See also copending application Ser. No. 07/866,763 (Attorney Docket No. 14875-1), the disclosure of which is incorporated herein by reference.

Radiofrequency ablation involves the application of radiofrequency energy, typically at a frequency in the range from about 250 to 1000 kHz, usually in the range from about 400 to 500 kHz, at a power level sufficient to raise the target tissue to a sufficiently high temperature for a time sufficient to induce tissue necrosis. Typically, the tissue temperature will be above about 45° C., usually being above about 60° C., but usually not exceeding about 105° C., and preferably being maintained below about 95° C. For such temperatures, the radiofrequency energy will typically be applied for time periods in the range from about 30 to 60 seconds, but time periods as short as 10 seconds and as along as 90 seconds also find use.

In order to deliver the radiofrequency energy to the desired target location within the heart, an intravascular catheter having a suitable electrode near its distal end will be percutaneously introduced, typically through the femoral vein or artery in the patient's groin. The distal tip of the catheter can then be manipulated by conventional means, typically through a previously introduced guiding catheter, until it reaches the interior of the heart. The electrode tip of the catheter will then be further manipulated so that it contacts the desired region within the interior of the heart chamber, typically the location of an accessory pathway, a location on the bundle of HIS, an arrhythmogenic site in the ventricular wall, or the like. Radiofrequency power will then be applied to the target location according to the method of the present invention, as described in more detail hereinafter. Preferably, the radiofrequency power will be applied using a radiofrequency generator and system of the present invention, also as described in more detail hereinafter.

Figure 1:
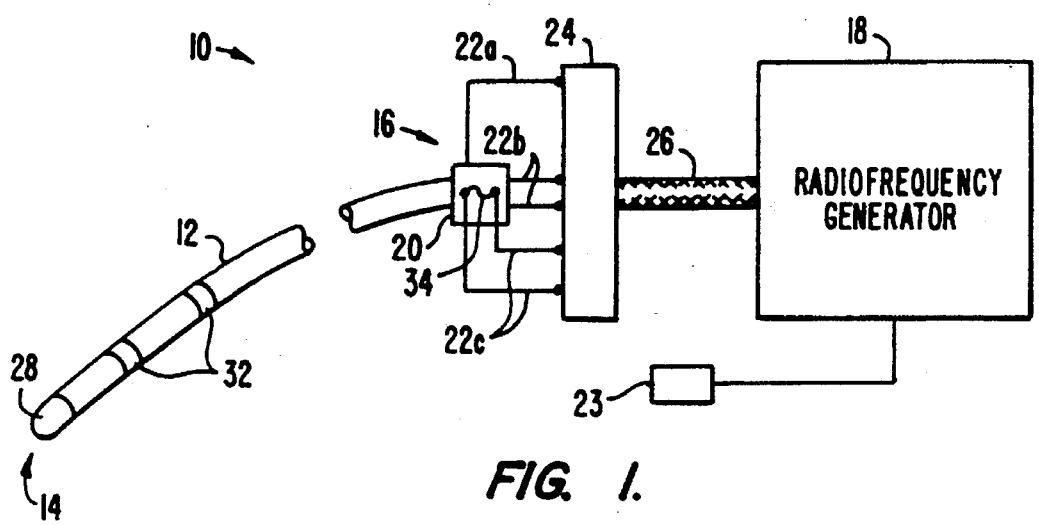
FIG. 1 is a schematic illustration of a system for radiofrequency ablation of cardiac tissue constructed in accordance with the principles of the present invention, comprising a catheter connected to a radiofrequency generator.

Referring now to FIG. 1, an exemplary radiofrequency ablation system 10 constructed in accordance with the principles of the present invention includes a catheter 12 having a distal end 14, a proximal end 16, and a radiofrequency generator 18 connected to the catheter as described below. The proximal ed 16 of the catheter 12 includes a proximal housing 20 having a plurality of connecting wires 22 that will normally terminate in a connector 24. The radiofrequency generator 18 is connected to the connector 24 through a cable 26. In this way, all active electrical components (as described hereinafter) of the catheter 12 may be removably connected to the radiofrequency generator 18 simply by plugging the catheter connector 24 into the cable 26.

Figure 2:
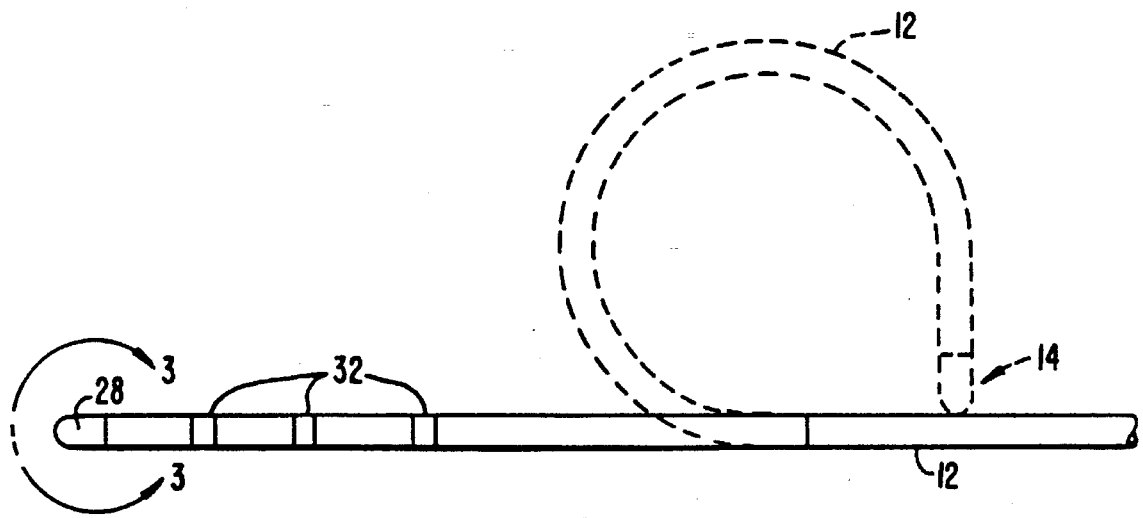
FIG. 2 is an enlarged view of the catheter of FIG. 1, with a curved tip shown in broken line.
Figure 3:
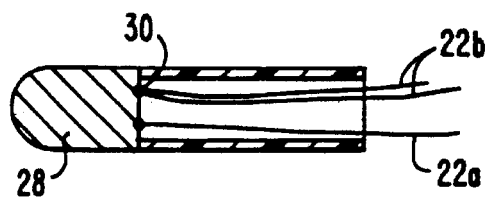
FIG. 3 is a detailed view of the catheter of FIGS. 1 and 2, shown in section.

Referring now to FIGS. 1–3, the catheter 12 includes an electrode 28 near its distal end, usually being at the distal tip, which is connected to a wire 22a which provide a monopolar power connection to the electrode 28 for applying radiofrequency energy from the generator 18, as will be described in greater detail hereinafter. An indifferent electrode 23 is separately connected to the generator 18 and permits attachment to the patient's skin surface to complete the circuit necessary for the application of RF energy as described below. A pair of wires 22b is connected to a temperature sensor 30 located on or in the electrode 28. Typically, the temperature sensor 30 will be a thermocouple consisting of a pair of dissimilar metals, usually copper and constantan which form a T-type thermocouple. The thermocouple wires 22b will also be connected to the radiofrequency generator 18 through the connector 24 and cable 26 so that they will be connected and disconnected as the catheter 12 is plugged and unplugged.

The catheter 12 may optionally include additional electrodes 32 axially spaced apart over the distal end 14. Electrodes 32 will usually be provided to permit ECG monitoring prior to, during, and/or after the radiofrequency ablation treatment. Additional connectors (not illustrated) will be provided so that the electrodes 32 may be connected to external monitoring equipment (not illustrated) through the connector 24 and cable 26. Usually, the radiofrequency generator 18 will include provisions for connecting such monitoring equipment to the catheter 12. Optionally, the electrodes 32 may be used to perform initial mapping to locate the accessory pathways in a generally conventional manner. These aspects of the catheter, however, do not relate directly to the present invention and will therefore not be described in detail.

Catheter 12 preferably includes a deflectable distal tip which permits lateral deflection, as illustrated in broken line in FIG. 2. A variety of control mechanisms (not illustrated) may be provided to effect such lateral tip deflection as described generally in the medical and patent literature. Preferred tip deflection mechanisms are described in copending application Ser. Nos. 07/866,383 and 07/867,241 (Attorney Docket Nos. 14875-2 and 14875-3), the disclosures of which are incorporated herein by reference.

A final pair of wires 22c illustrated in FIG. 1 are connected to a fuse 34 disposed within the proximal housing 20. The fuse 34 is provided to permit verification by the radiofrequency generator 18 that the catheter 12 has not been previously used. Reuse of the catheter 12 is undesirable since a previously used catheter can be a source of infection and will be generally less reliable than a new catheter. The verification procedure will be described in more detail hereinafter.

Figure 4:
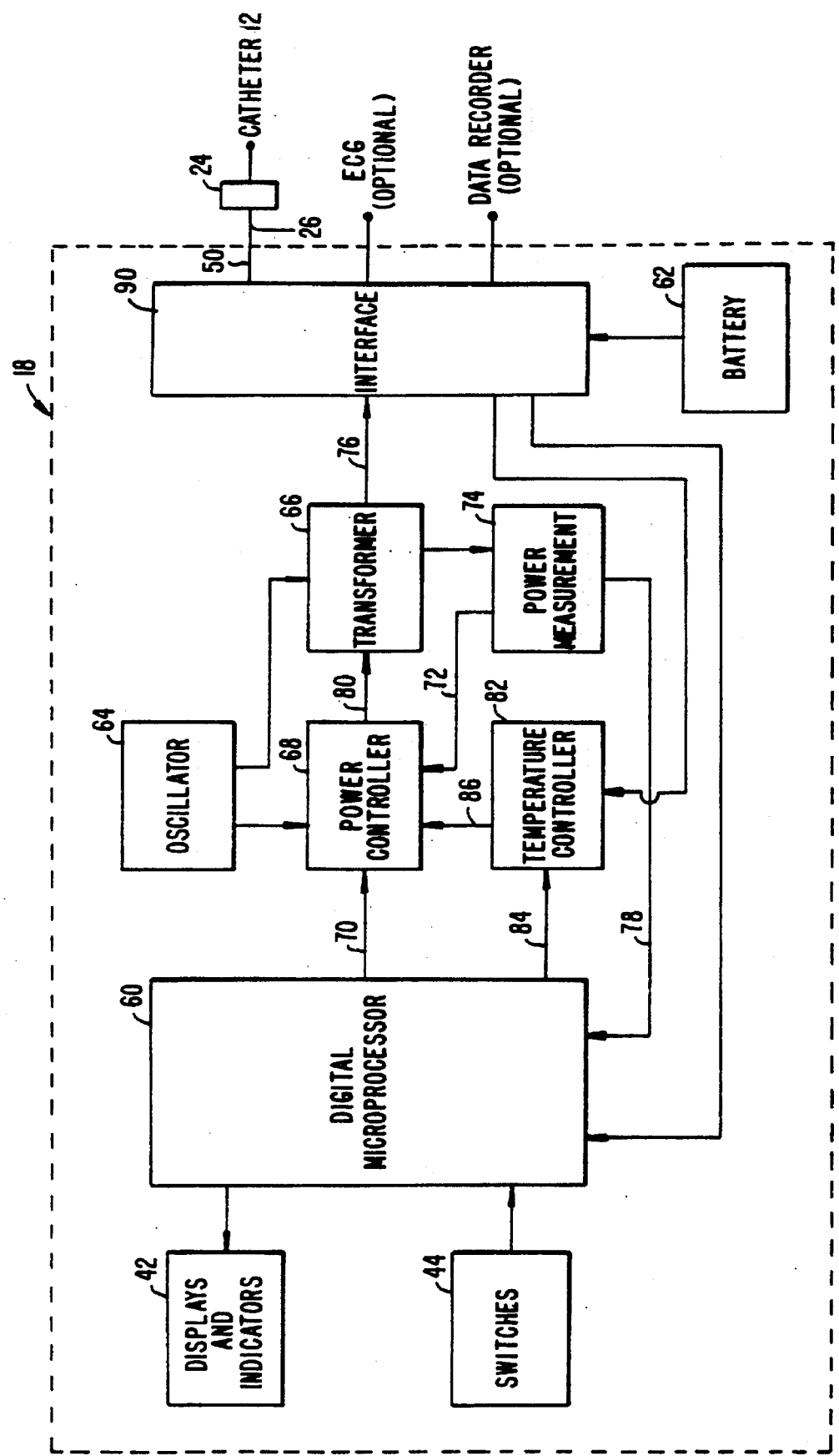
FIG. 4 is a block diagram of the circuitry of a radiofrequency generator constructed in accordance with the principles of the present invention.
Figure 5:
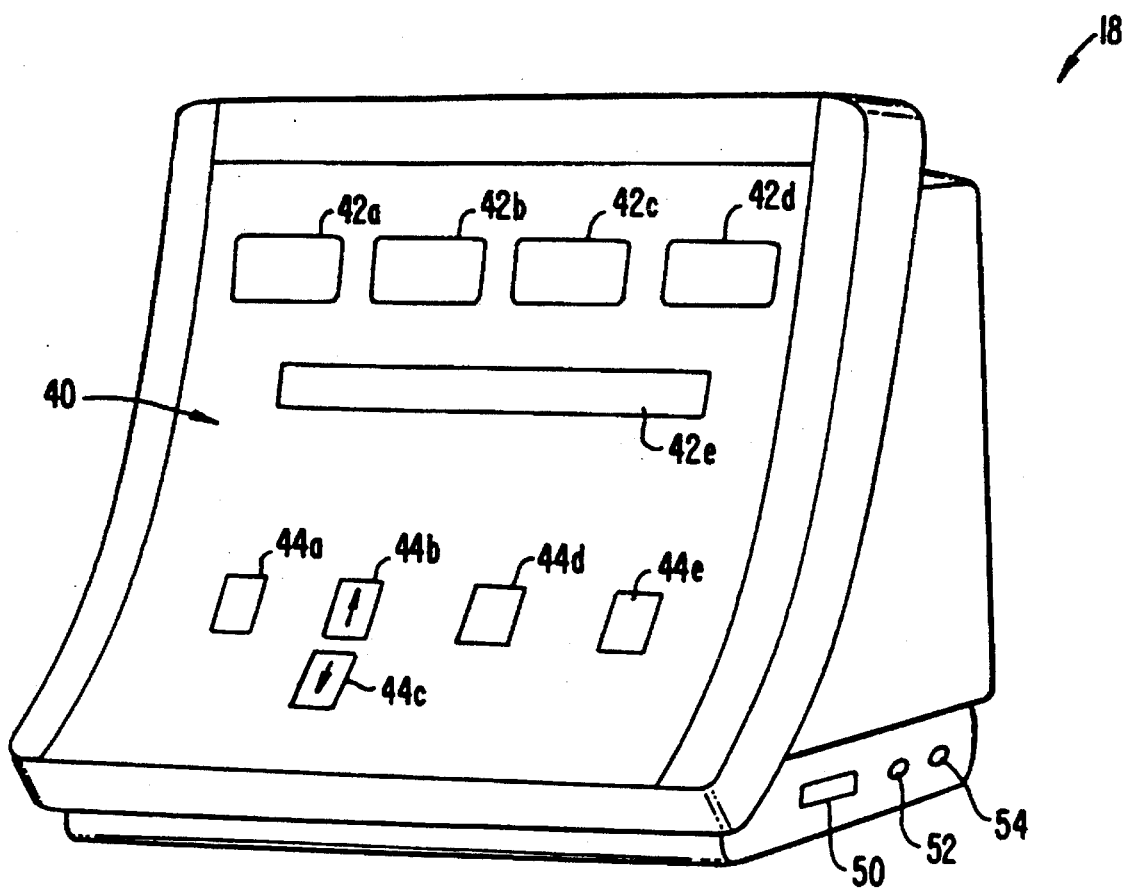
FIG. 5 illustrates the exterior of a power supply system constructed in accordance with the principles of the present invention.

Referring now to FIGS. 4 and 5, the radiofrequency generator 18 of the radiofrequency ablation system 10 will be described in more detail. Radiofrequency generator 18 includes a user interface panel 40 having a plurality of displays and indicators 42, switches 44 and legends (not illustrated), to permit the operator to monitor and control delivery of power to the catheter 12, as will be described in greater detail hereinafter. In particular, the indicators 42 and switches 44 permit monitoring and control of the amount of radiofrequency power delivered to the catheter 12 by radiofrequency generator 18. The panel 40 includes a first display 42a which provides a continuous digital readout of the actual radiofrequency power being delivered (usually calibrated in Watts). A second. display 42b shows the actual electrode temperature measured by the thermocouple 30 (FIG. 3). A third display 42c shows the calculated impedance (based on measured current and voltage) between the catheter ablation electrode 28 and an indifferent electrode during the delivery of radiofrequency energy. The indifferent electrode is attached to the patient and provides a return path to complete the circuit to the tip electrode 28. A sudden rise in impedance indicates that coagulum has formed on the tip, which should be removed. A fourth display 42d provides an indication of the time that radiofrequency power has been delivered during an ablation procedure.

The panel 40 further include an alphanumeric display 42e which presents additional information to the user, depending on the operational mode selected as described below. Such information includes the set point for either temperature (in ° C.) or power (in Watts), depending on the control mode. The display 42e can further set forth the total number of cycles, i.e. the number of times that power supply to the ablation electrode 28 has been initiated. The display 42e can further indicate total treatment time, i.e. the total elapsed time that the radiofrequency power has been delivered from the time power to the generator 18 was turned on. Finally, the legend 42e will indicate the available set point range for power, temperature, or time, depending on the variable which is being set within the system (when a set point is changed).

The alphanumeric 42e can further provide user warnings, including excessively high temperature, unacceptable catheter (when a catheter having a broken fuse 34 is connected to the radiofrequency generator 18, as described below), excessively high impedance, low impedance, and excessively high power. Finally, a legend (not illustrated) will indicate when the battery charge has become low, typically when it reaches 25% of capacity. Conveniently, a tone warning signal will be provided whenever any warning is being displayed.

A switch 44a is provided in order to select the control mode, i.e., either power or temperature. A particular variable (temperature or power) will be adjusted by raising or lowering the set point using the appropriate up, or down switch 44b or 44c. The user presses and holds switch 44d and increases the time set point by pressing switch 44b or decreases the time set point by pressing switch 44c. After initiation, the power will be delivered for the total time thus set. The value of the particular variable set point (and allowable range) is displayed on alphanumeric display 42e as the set point is being adjusted.

Switch 44e controls the delivery of RF power. When the RF power generator 18 is first turned on, a legend OFF (not illustrated) is lit. Switch 44e must be pressed to put the unit in standby which also activates an optional foot pedal (not illustrated). Once in standby mode, pressing switch 44e causes RF power to be delivered until either the switch 44e is again pressed or the time set-point is reached, at which time the unit returns to standby. If a warning condition occurs (i.e., high power or high impedance), the unit goes to OFF mode and the optional foot pedal is deactivated.

A main off and on switch is provided on the top of the radiofrequency generator 18. A catheter connector 50, an indifferent electrode connector 52, and a foot pedal connector 54 are provided on the right side of the radiofrequency generator 18. The catheter connector 50 permits plugging in of the catheter connector 24 to cable 26 to provide the necessary connections between the electrical components of the catheter and the generator 18. The foot pedal connector permits connection of a pneumatic foot pedal which allows the treating physician to control the application of radiofrequency power by depressing and holding the foot pedal.

Additional connections on the radiofrequency generator 18 will usually include an ECG connector, an analog output connector which permits output to a multi-channel chart recorder for recording radiofrequency power, impedance between the ablation electrode and indifferent electrode, and ablation electrode temperature. An additional connector will usually be provided to permit connection of the internal microprocessor to an external computer to monitor and temporarily override programming in the PROMS. The connector will usually be a conventional RS-232 connector which is compatible with standard IBM-type personal computers. A switch may also be provided to permit the operator to set the volume level of the tone during the RF ablation. Finally, a TUV connector will be provided for connection to an external ground.

Referring now to FIG. 4 in particular, the front panel displays and indicators 42 and switches 44 will be connected to a digital microprocessor 60, such as an INTEL 80C 186, which permits interface between the user and the remainder of the electrical components of the system. In particular, the microprocessor 60 provides for continuous monitoring of power, current, voltage, temperature, impedance, and battery level. As necessary, the microprocessor will provide this information to the appropriate display and/or indicator 42 on the front panel 40. Additionally, the microprocessor 60 permits the user to select the control mode (either constant temperature or constant power) and to input the power set point, temperature set point, and timer set point to the system.

The primary source of power for the radiofrequency generator 18 is a battery 62, typically a 12 V battery rated at 7.2 ampere-hours. A back-up battery (usually a lithium cells not illustrated) will be provided to provide sufficient power-to the microprocessor 60 to maintain desired memory functions when the main power from battery 62 is shut off.

A crystal-locked radiofrequency oscillator 64 generates the switching pulses which drive both the power transformer 66 and the power controller 68. Power controller 68 is an analog controller which operates by pulse-width modulation by comparing a power set point signal 70 (from microprocessor 60) with an actual power signal generated by a power measurement circuit, typically a torroidal transformer coupled to the power output 76 from the transformer 66. The power measurement component 74 multiplies the output current and voltage and provides the resulting actual power signal to both the power controller through line 72 and the microprocessor through line 78. Separate analog comparator circuits (not illustrated) are provided for monitoring the output of the power measurement component 74 in order to shut-off current to the output transformer if the power exceeds a limit, typically 55 watts.

Power transformer 66 includes a center tap which receives the output 80 of the analog power controller 68. Secondary winding provides for continuous monitoring of the applied voltage in order to permit the power calculations by power measurement circuit 74.

Figure 12A:
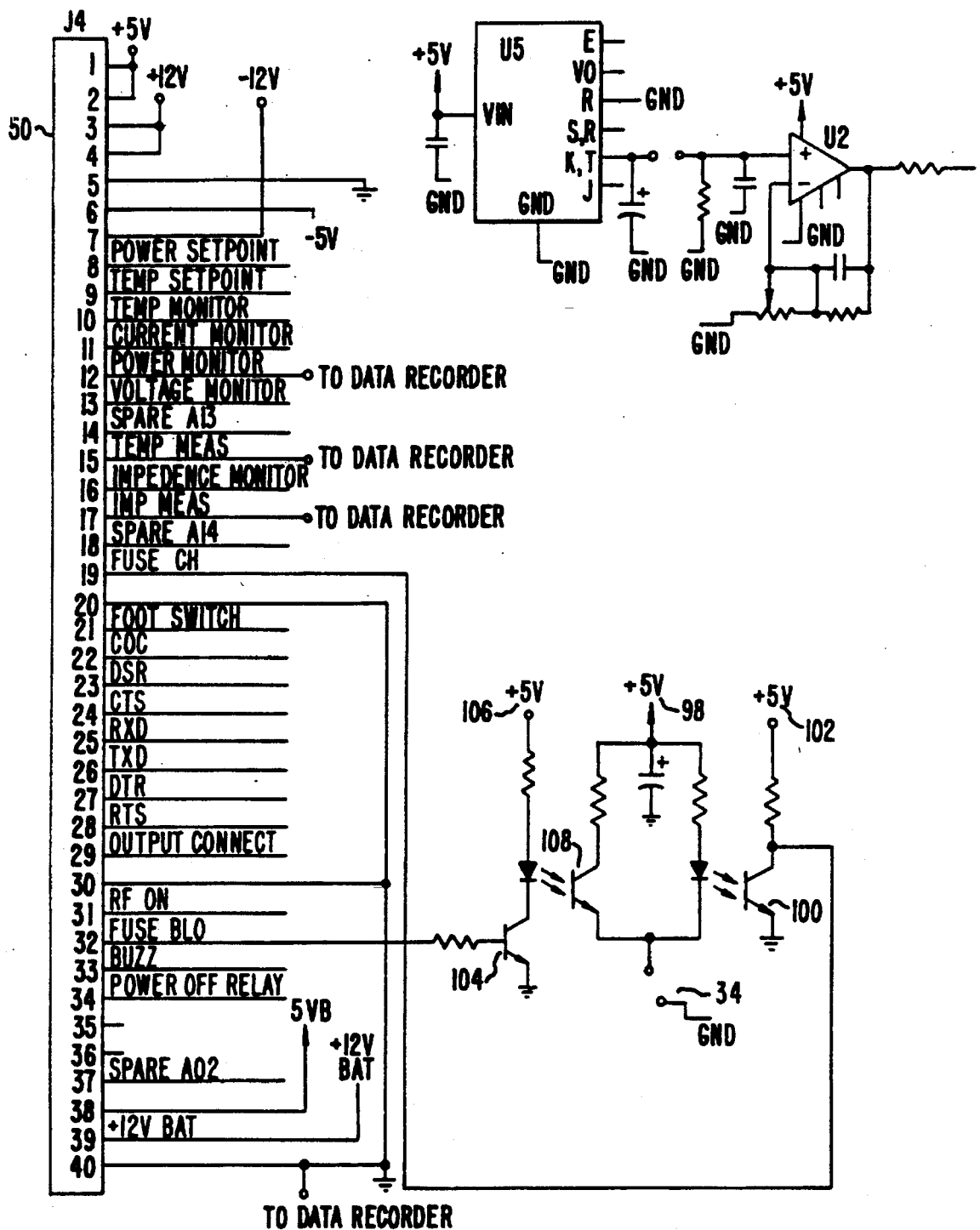
Figures 12, 12B:
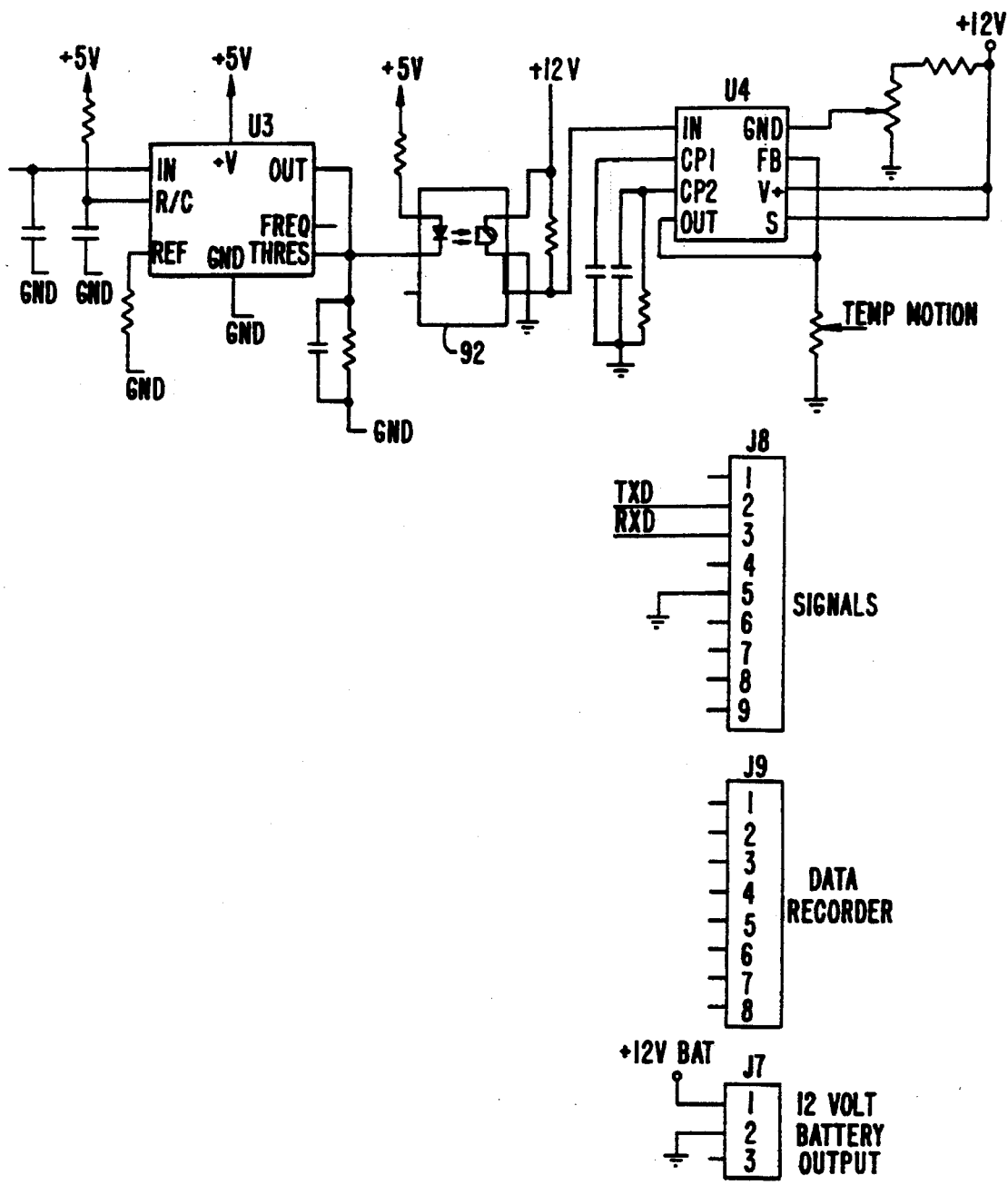
Figure 12C:
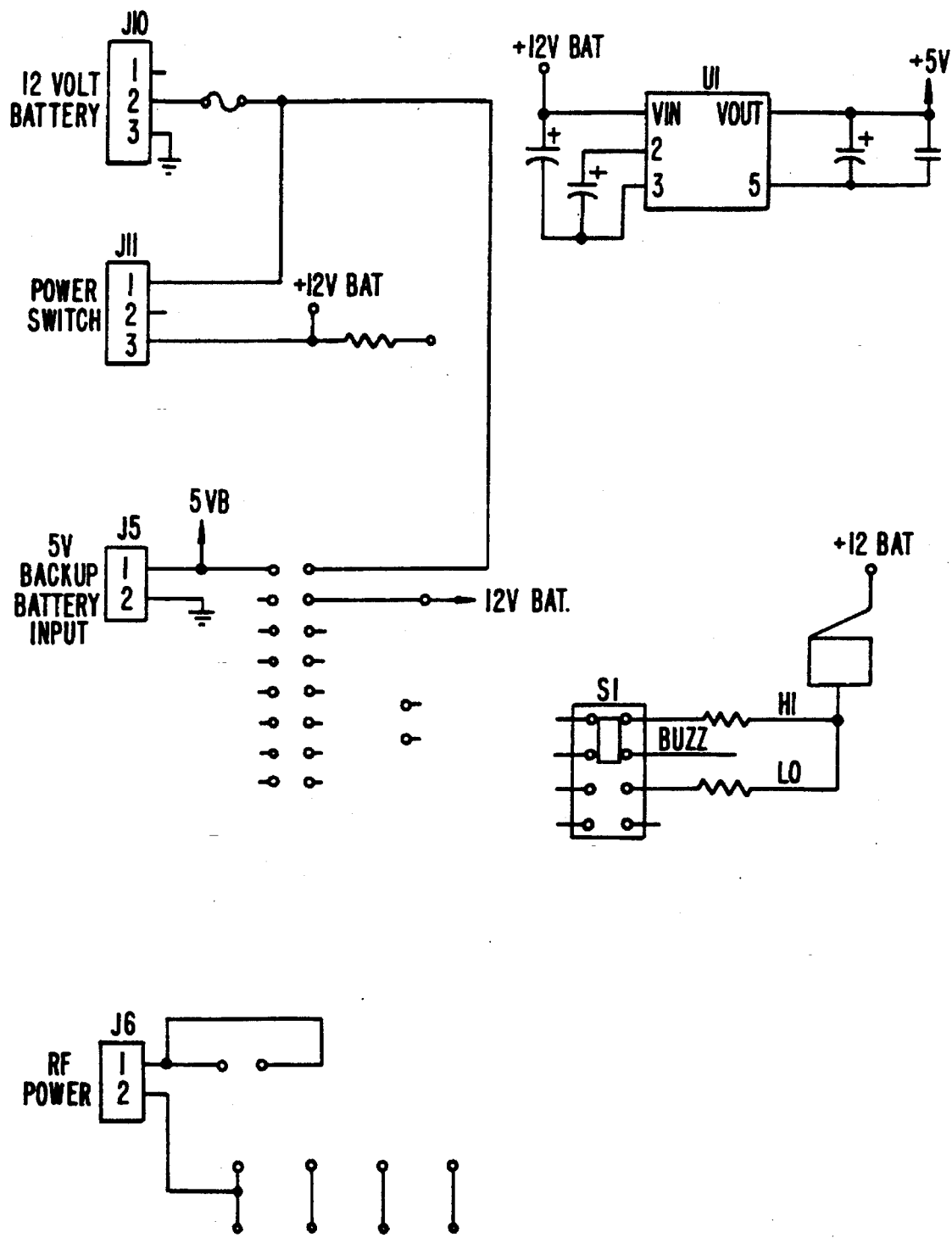

In a preferred aspect of the present invention, an analog temperature controller 82 is provided to permit operation in a temperature control mode. A temperature set point is delivered to the temperature controller 82 from the microprocessor 60 through line 84. Analog controller 82 operates on a proportional control mode, producing a power set point 86 which is fed to the power controller 68. Power set point 86 replaces the set point 70 when the system is in temperature control mode operation. The analog power controller 68 thus acts as a cascade control loop in a two-stage temperature control protocol. It has been found that such two-stage analog control permits precise and very fast control of power to maintain the desired temperature set point at the ablation electrode 28. In particular, the control scheme permits very rapid temperature rise to the desired temperature set point with minimum overshoot and very close temperature maintenance throughout the duration of the radiofrequency ablation cycle. The temperature will usually be maintained within ±5° C. of the set point, more usually being maintained to within ±2° C. of the set point. Separate analog comparator circuits 90, illustrated in FIG. 12, are provided for monitoring the temperature of the thermocouple 30 in order to shut-off current to the output transformer if the temperature exceeds a limit, typically 105° C.–110° C.

All external connections to the radiofrequency generator 18 will be made through an interface board 90. The interface board 90 permits connection of the main battery 62 and back-up battery (not-illustrated), as well as the catheter connector 50, the ECG connector, the data recorder connector, and the like. Connection of the thermocouple will be optically isolated from the internal components of the radiofrequency generator 18 by optoisolator 92, shown in FIG. 12. The data recorder outputs on the RF generator 18 may be optically isolated if necessary to reduce signal noise. Such isolation provides both patient safety as well as isolation of the internal components of the generator 18 from the radiofrequency power which is being delivered to the patient.

The detailed circuitry necessary to construct the radiofrequency generator 18 is set forth in detail in the appendix attached to this application. The appendix includes six circuit diagrams, where each circuit diagram is labeled to indicate the components which are included on that diagram.

Figure 6A:
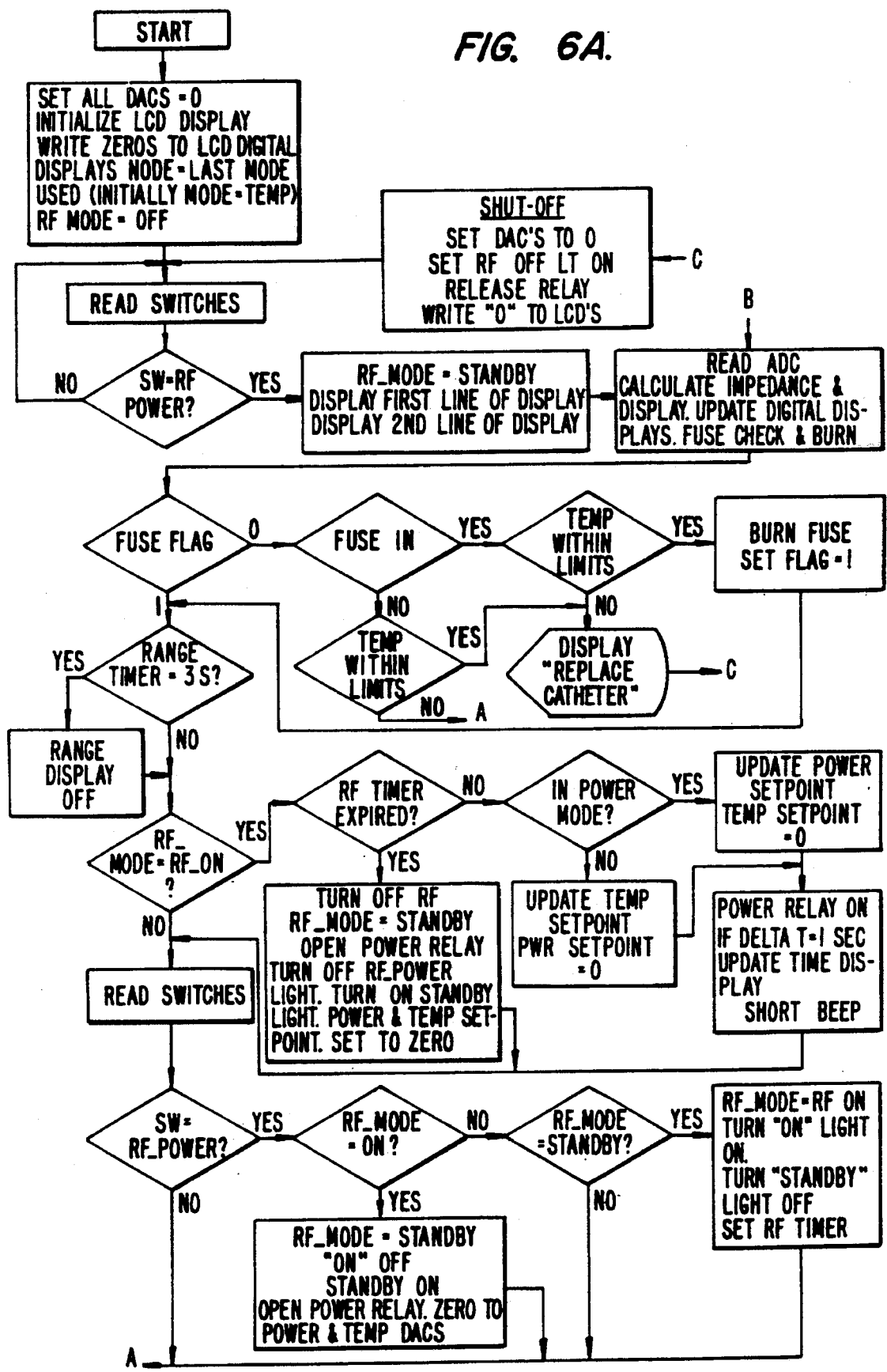
FIGS. 6A and 6B illustrate a flow chart of the operating program of the microprocessor-controlled power system of the present invention.

Operation of the microprocessor is schematically illustrated in the flow sheet included in FIGS. 6A and B.

The relationship of the microprocessor 60 to other hardware elements of the RF ATAKR system are shown in FIG. 4. The variable inputs to and outputs from the microprocessor 60 are identified as follows:

| MICROPROCESSOR | |
| --- | --- |
| From catheter 12: | To catheter 12: |
| Tip electrode temperature Impedance (tip electrode to indifferent electrode) | Power to tip |
| From power controller 68: | To power controller 68: |
| Power level Voltage | Start/stop RF power |

| MICROPROCESSOR | |
|---|---|
| Current From panel face 40: | To panel face 40: |
| Control mode | System status (on, off, standby) |
| Temperature set point | Audible alarm |
| Power set point | Visual alarm |
| Timer set point | Displays (power, temp., impedance, |
| RF Power delivery | etc.) |

The microprocessor 60 performs the system control function by reading the user, catheter, and generator input values and providing corresponding power on/off commands to the RF power controller 68 and system status and alarm information to the user. The input values for temperature, current, and voltage originate as analog signals and are converted to digital (via digital/analog converters (DAC's)) for the microprocessor. Impedance and power are calculated from current and voltage. Timing is maintained by onboard clock.

Default values of the system are maintained in two ways. Preset default settings are in effect upon initial use and if the backup battery fails. These present default settings are as follows:

| Setting | Default Condition |
|---|---|
| Control Mode | Temperature |
| Temperature set-point | 70° C. |
| Power set-point | 20 Watts |
| Time set-point | 30 seconds |

If the user changes these settings, the last settings entered become the default settings on system power-up providing the backup battery does not fail.

Specific safety features incorporated in the programming of the microprocessor 60 include the following.

In both temperature and power power control mode, RF power is applied to the catheter only during the selected cycle time and only when the impedance is within a preset range (typically 25 to 250 ohms). Additionally, power must be below a preset maximum (typically 55 watts maximum), and the temperature must be below a preset maximum (typically to 105° C. when operating in temperature control mode). Also, the catheter must not have been previously used as described earlier.

Figure 7A:
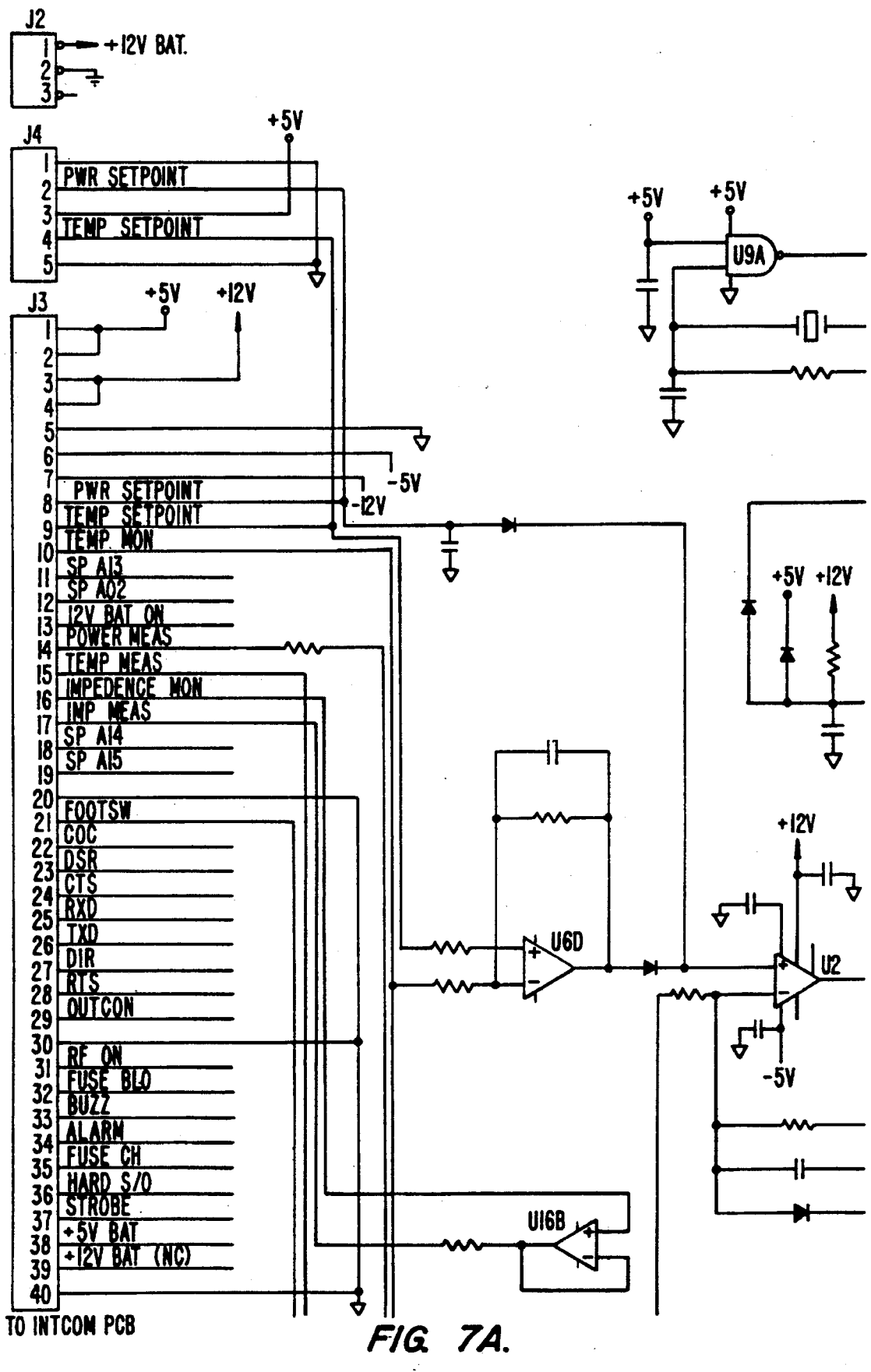
Figure 7B:
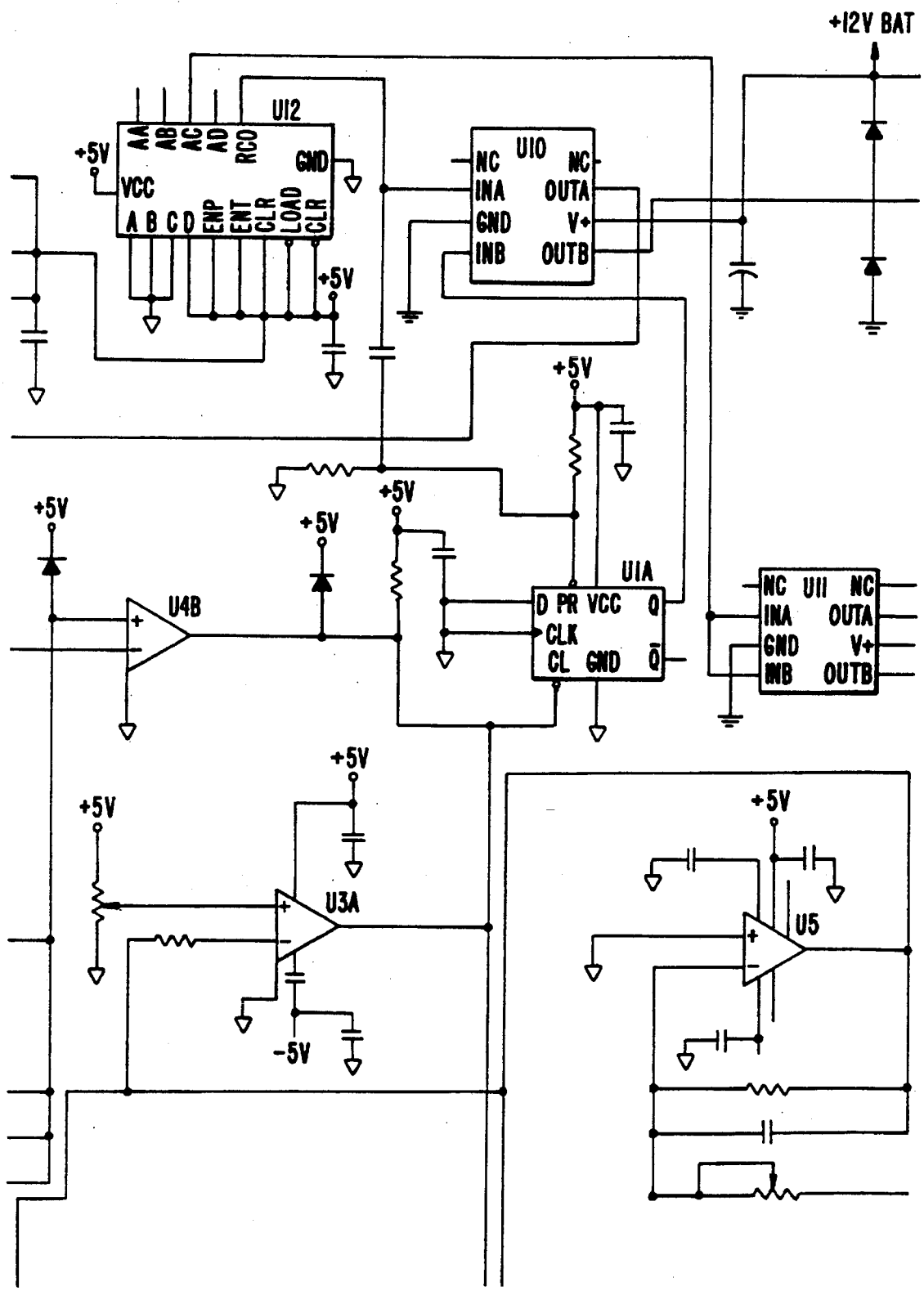
Figure 7C:
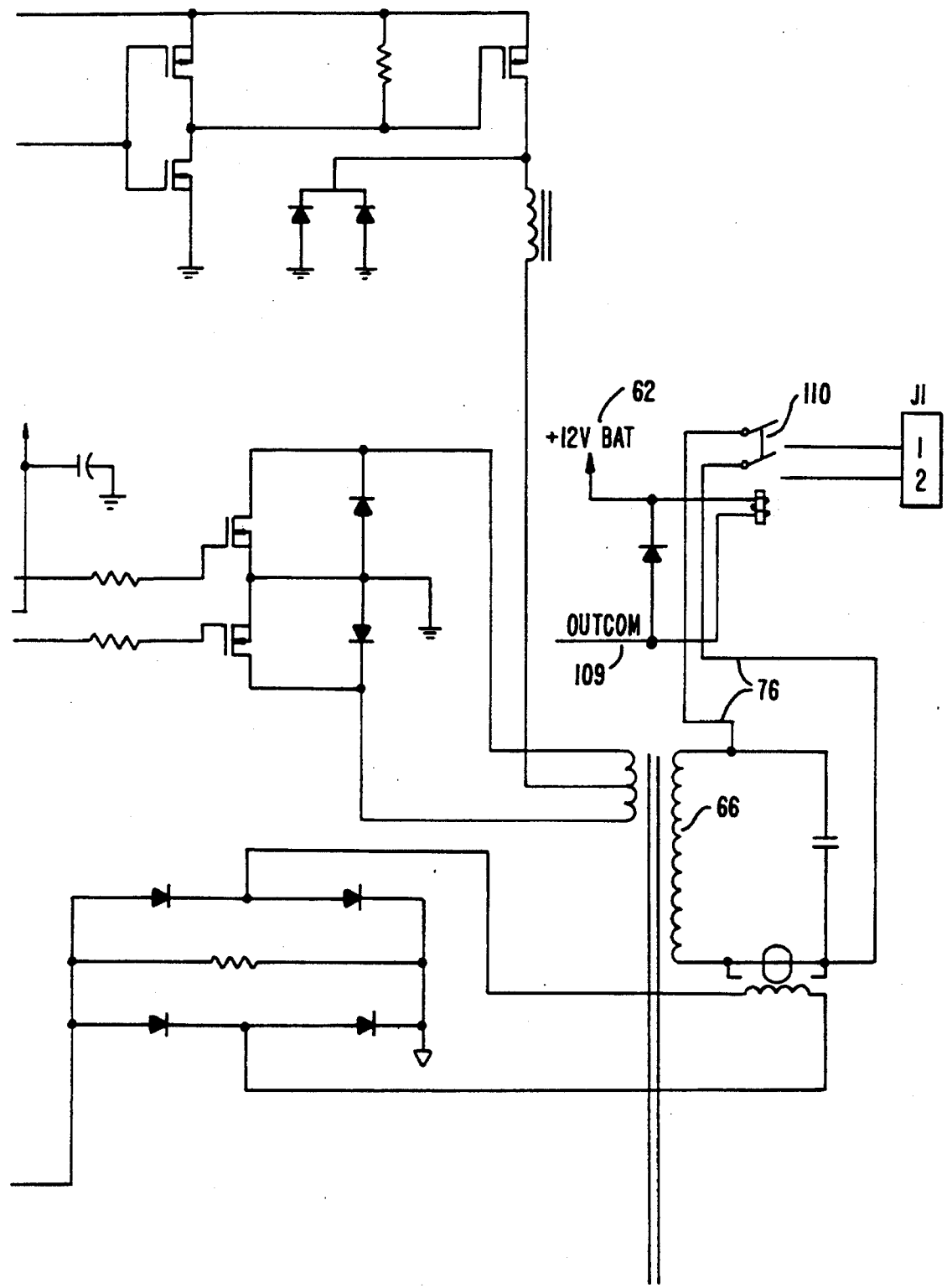
Figure 7D:
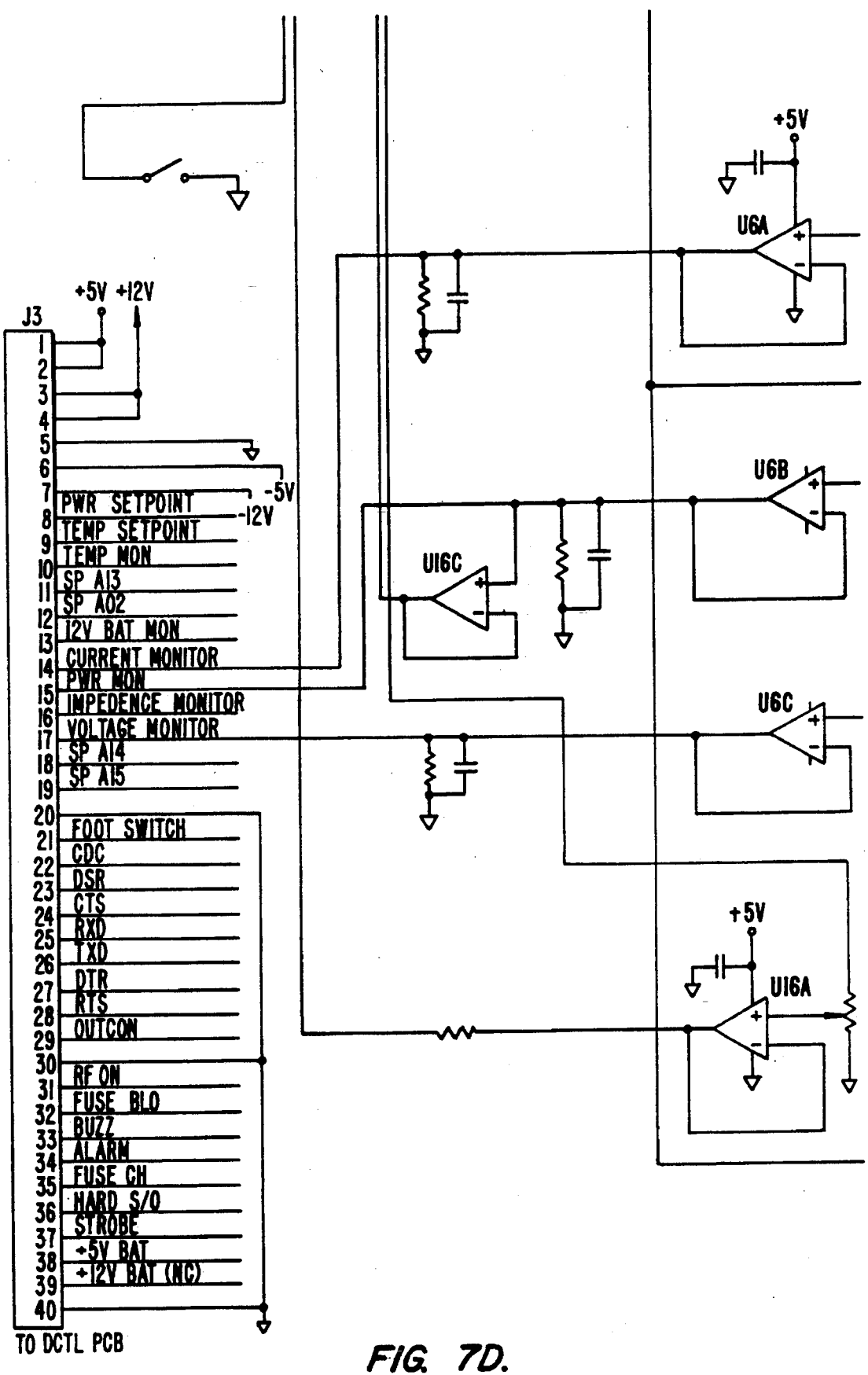
Figure 7E:
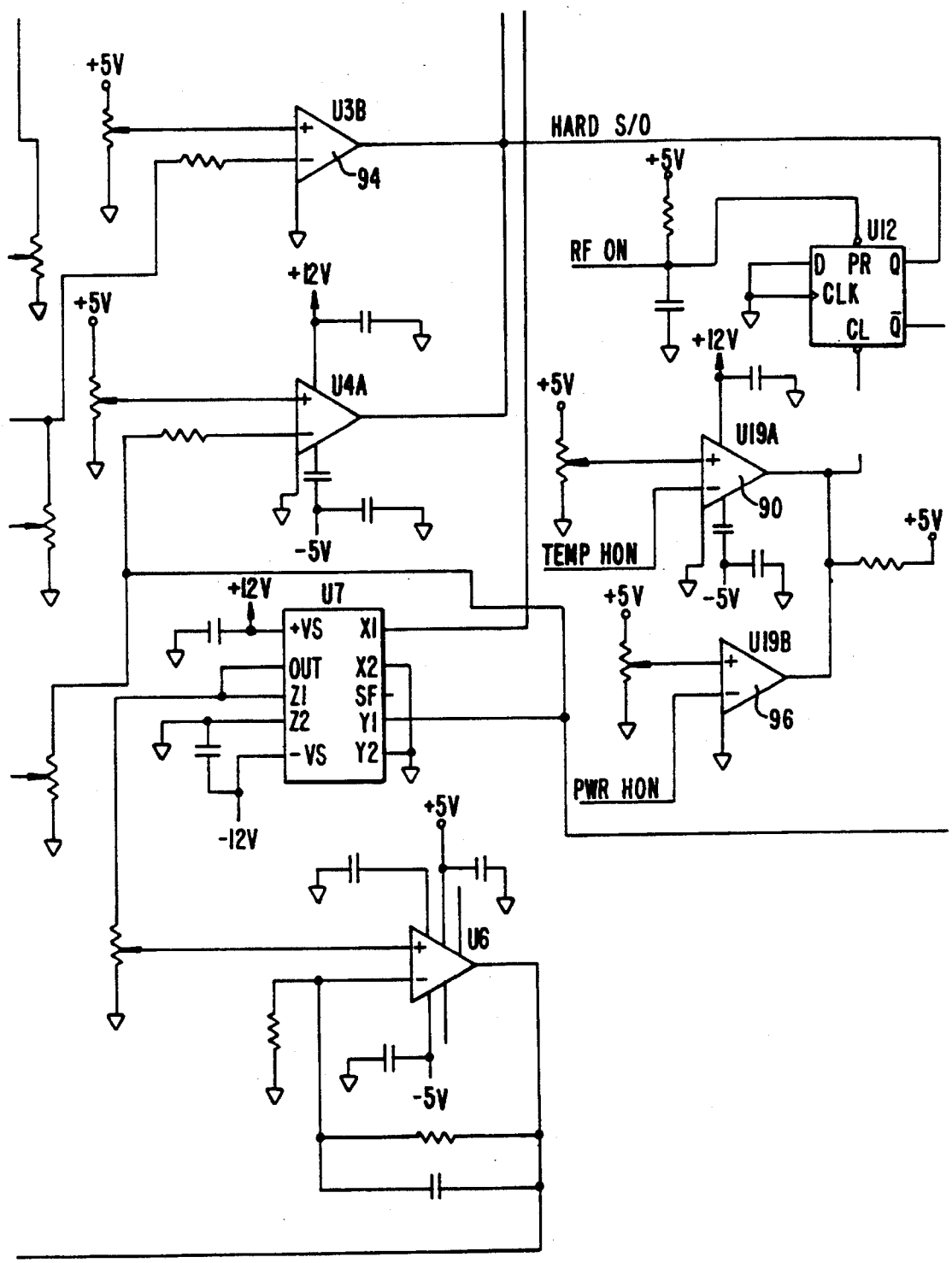
Figures 7, 7F:
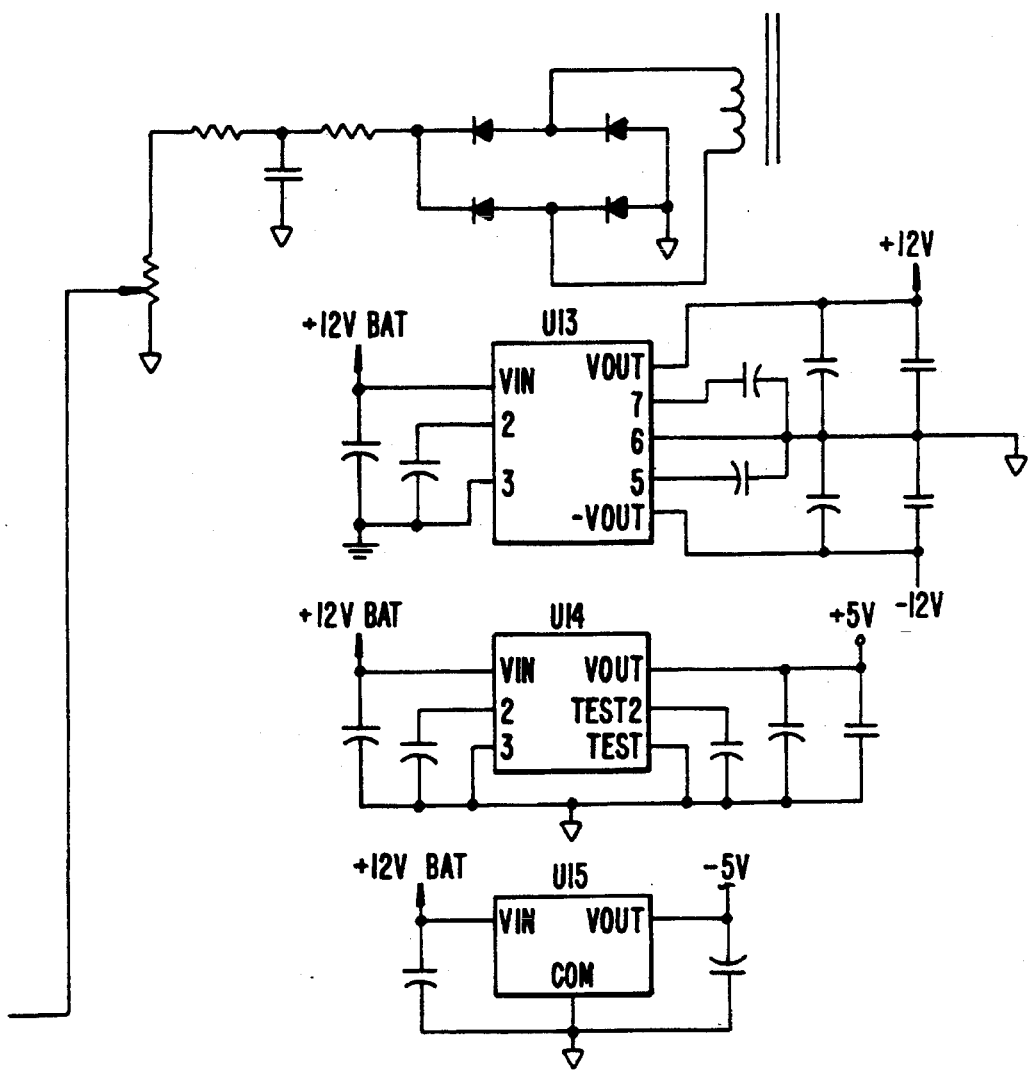
Figures 8, 8A:
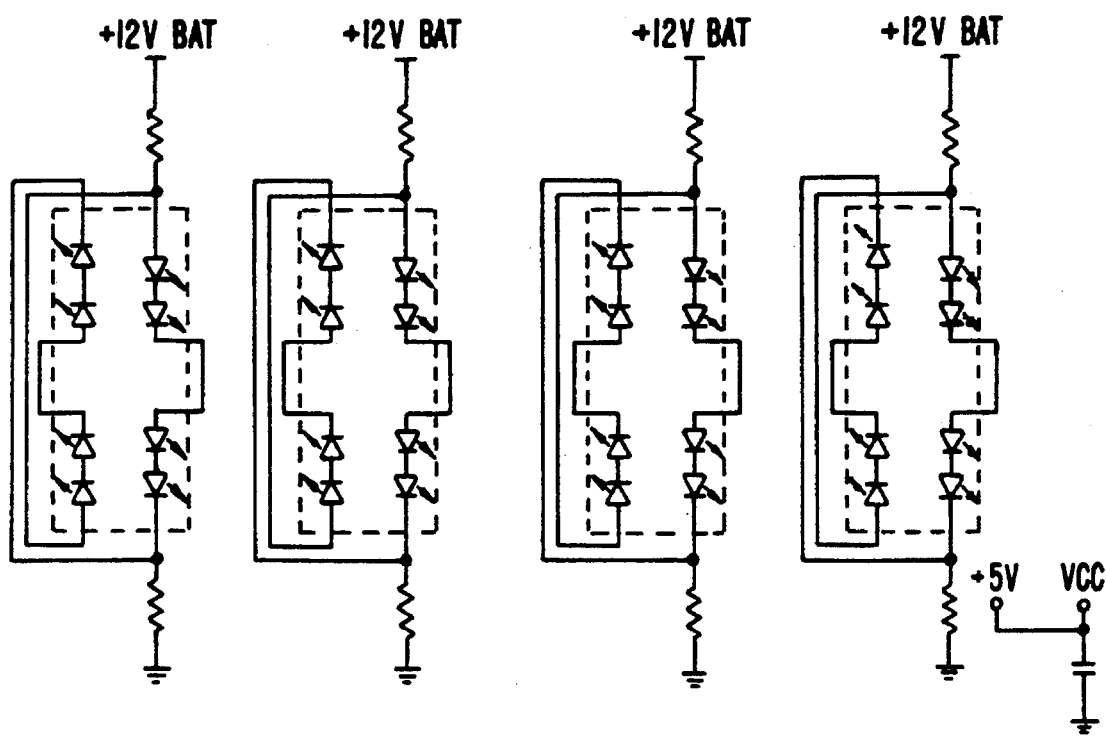
Figure 8B:
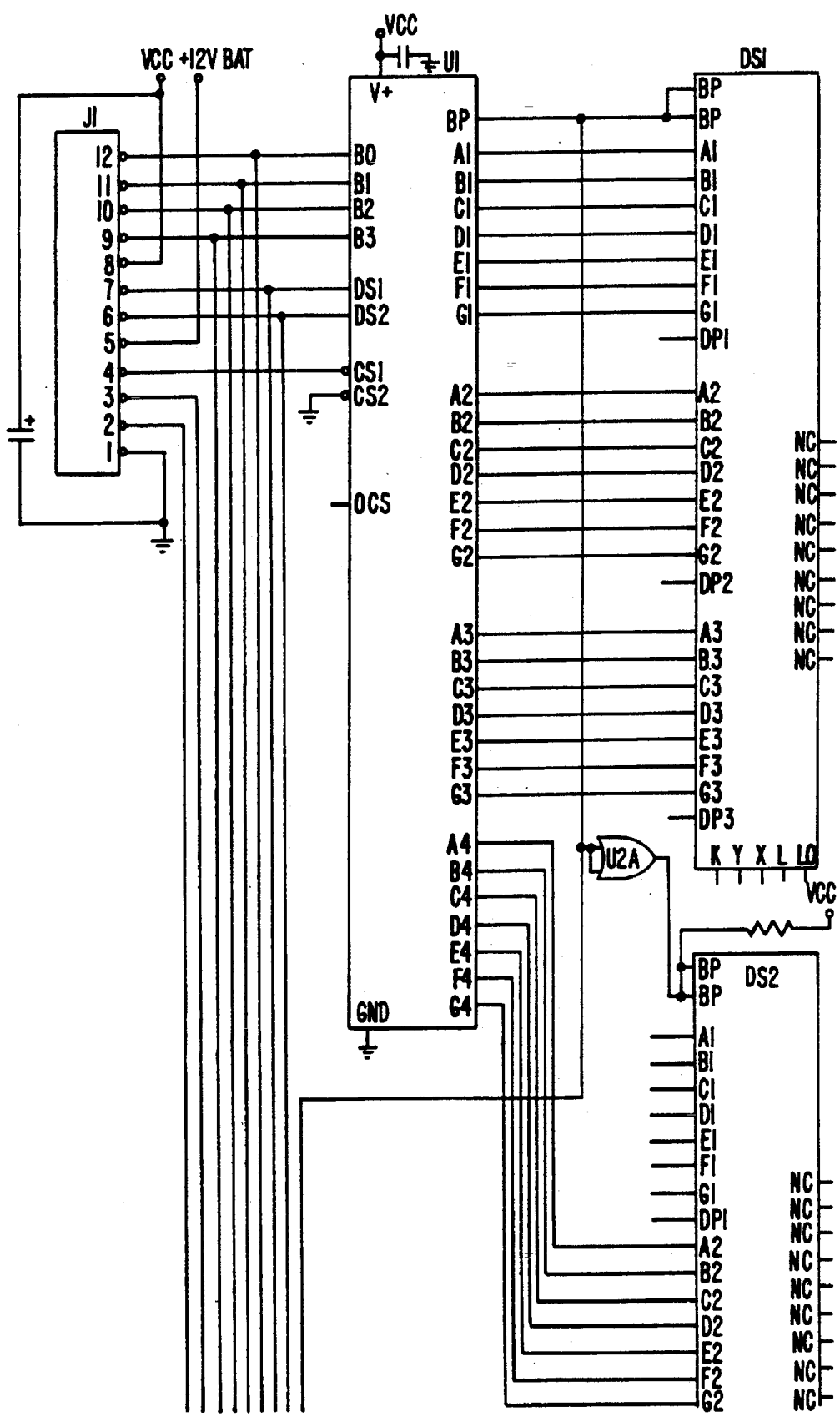
Figure 8C:
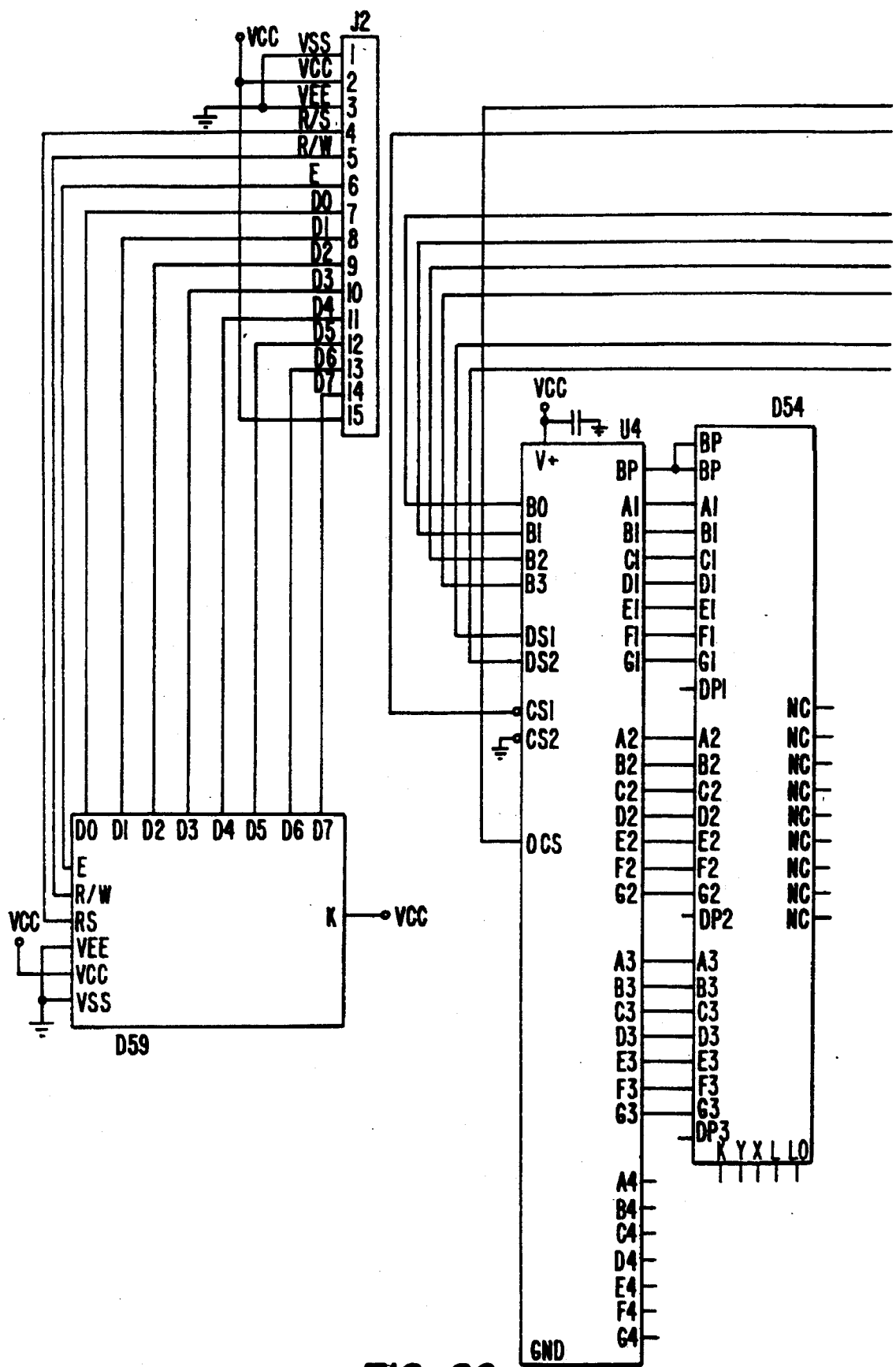
Figure 8D:
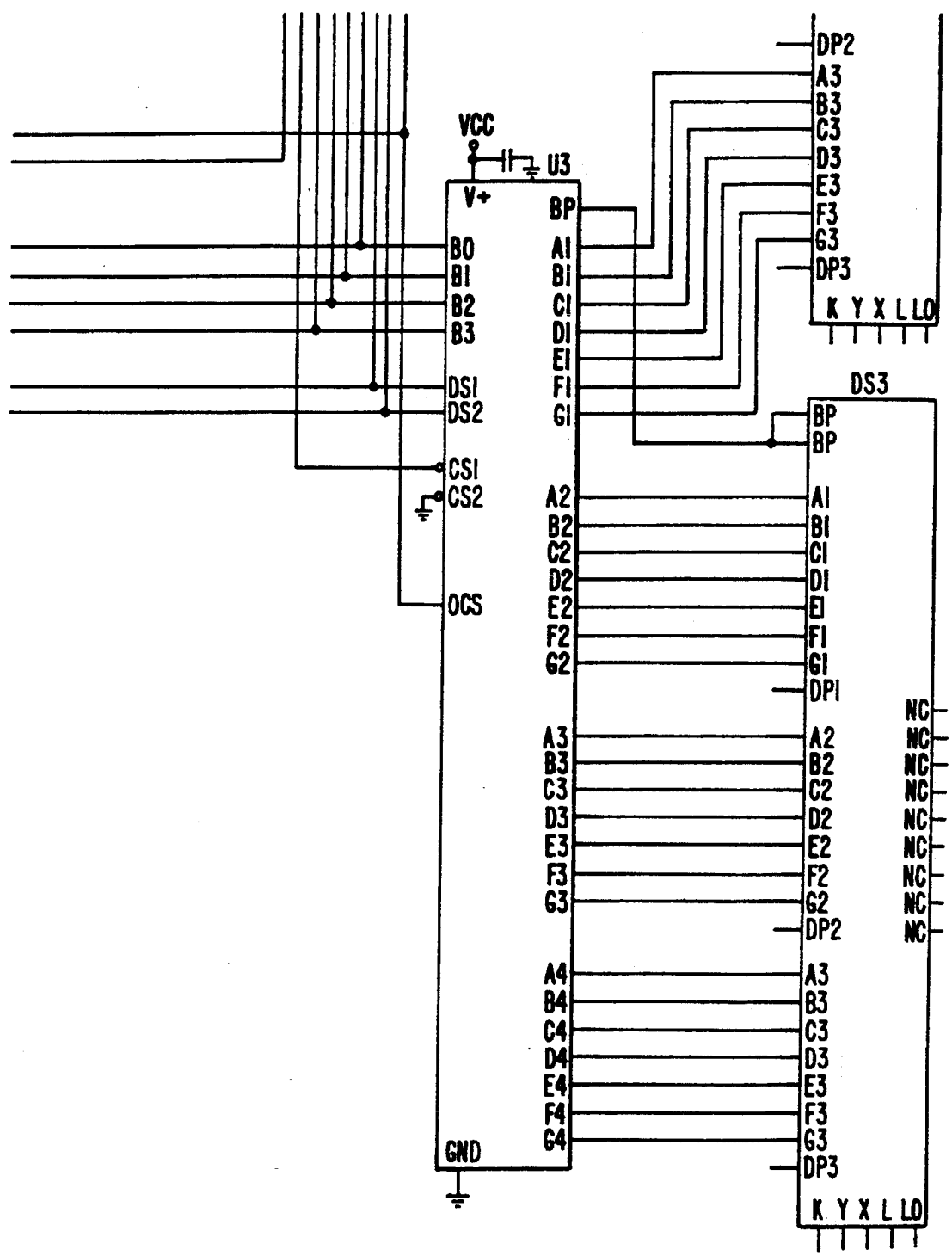
Figure 9A:
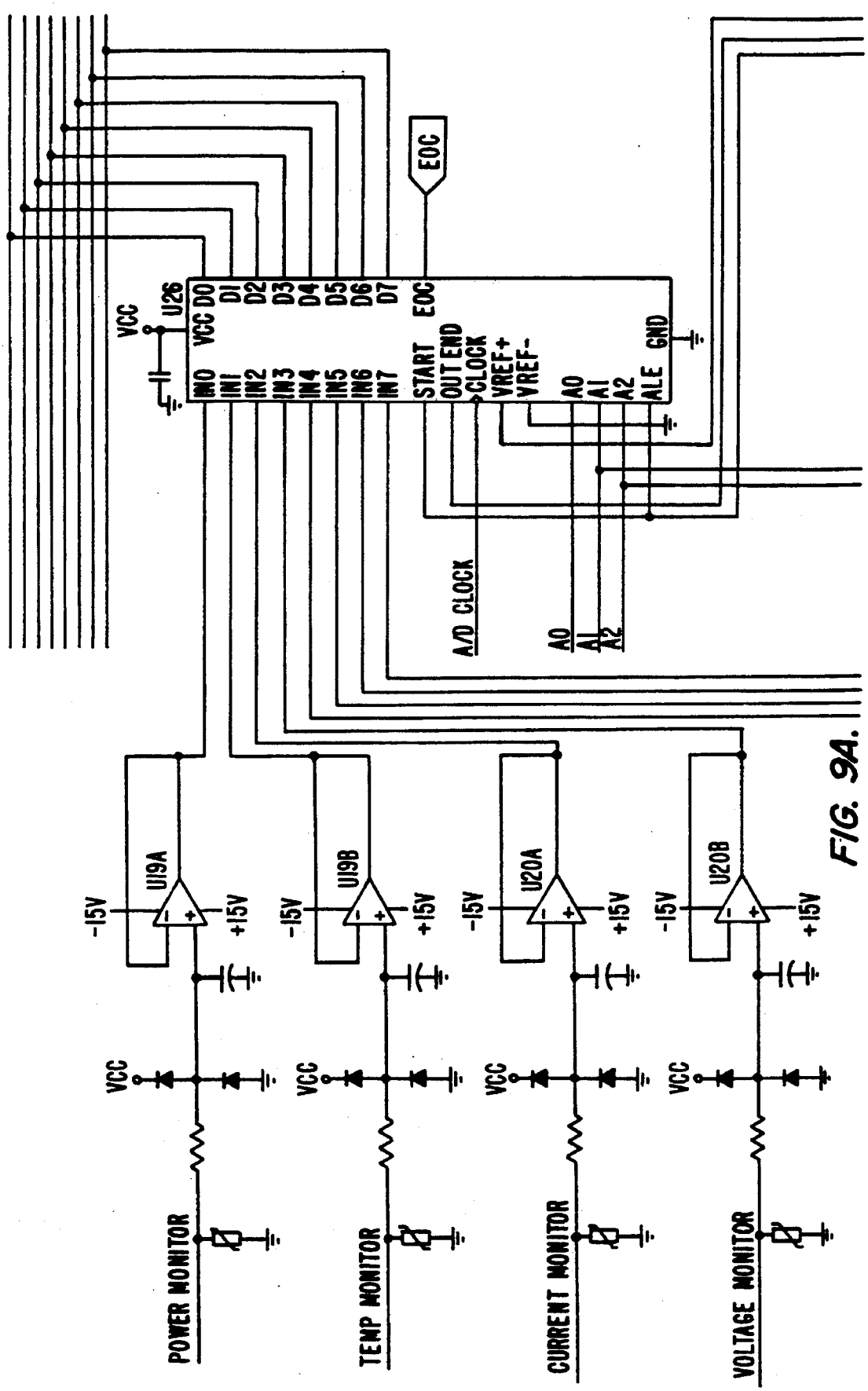
Figure 9B:
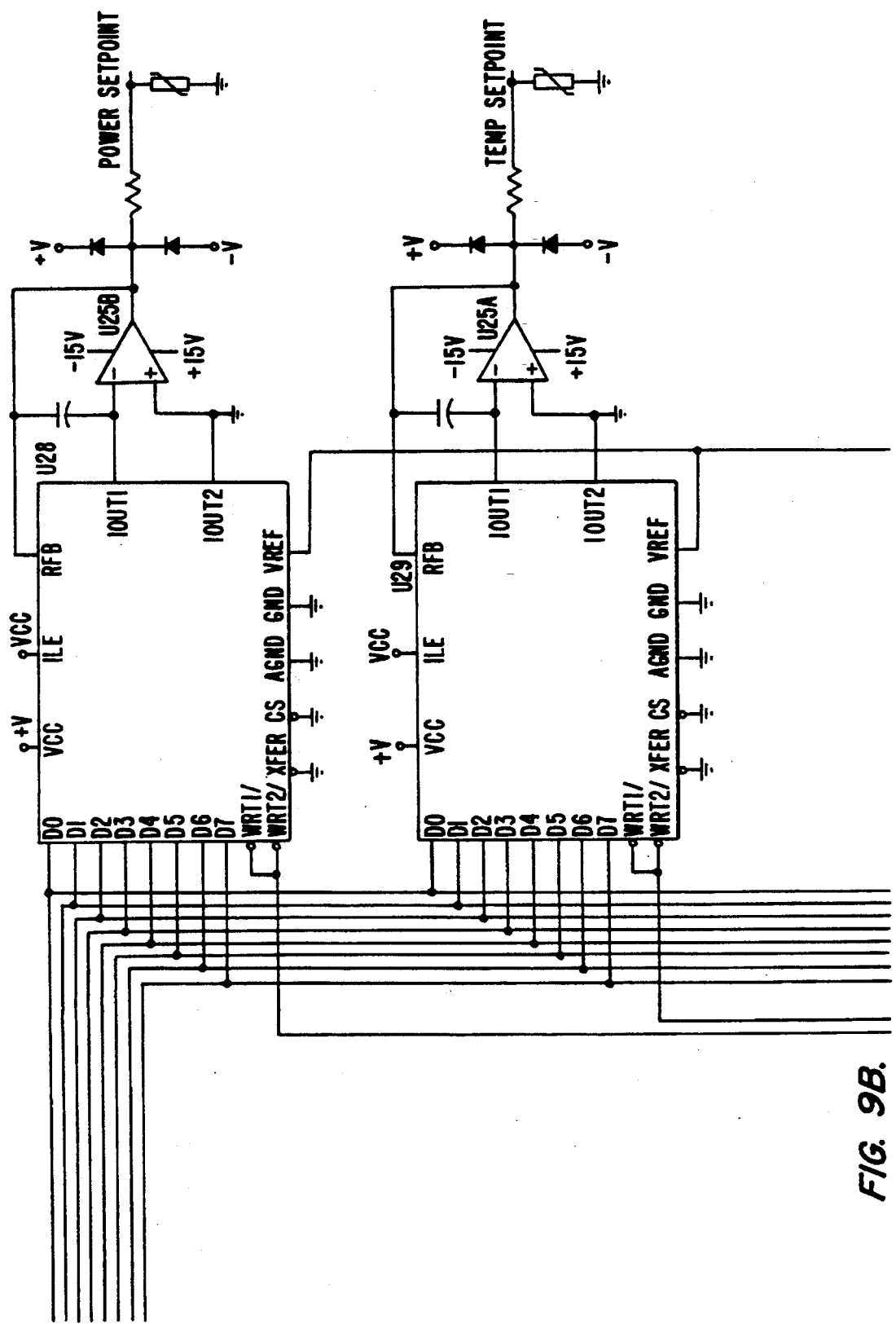
Figure 9D:
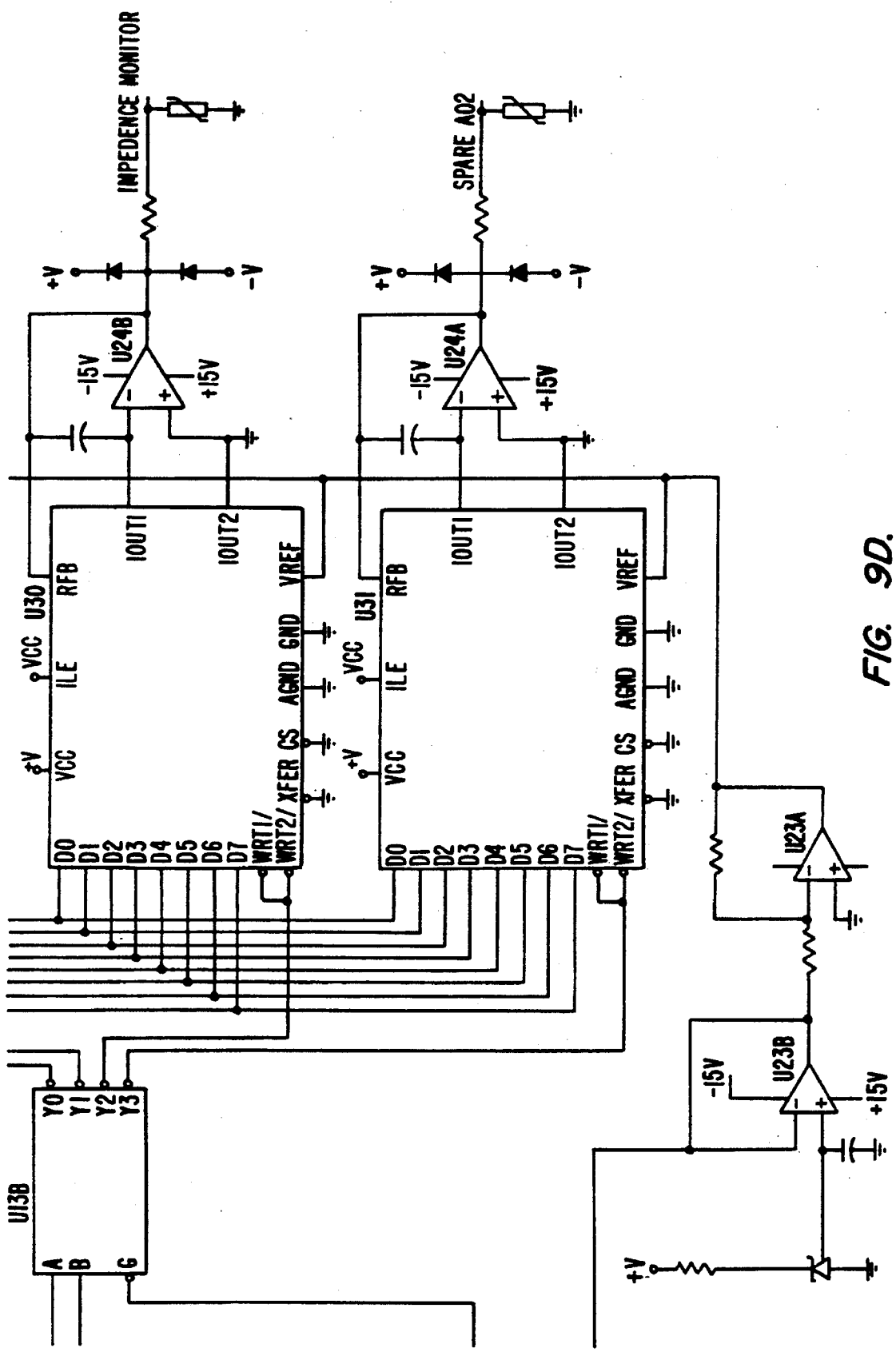
Figure 10A:
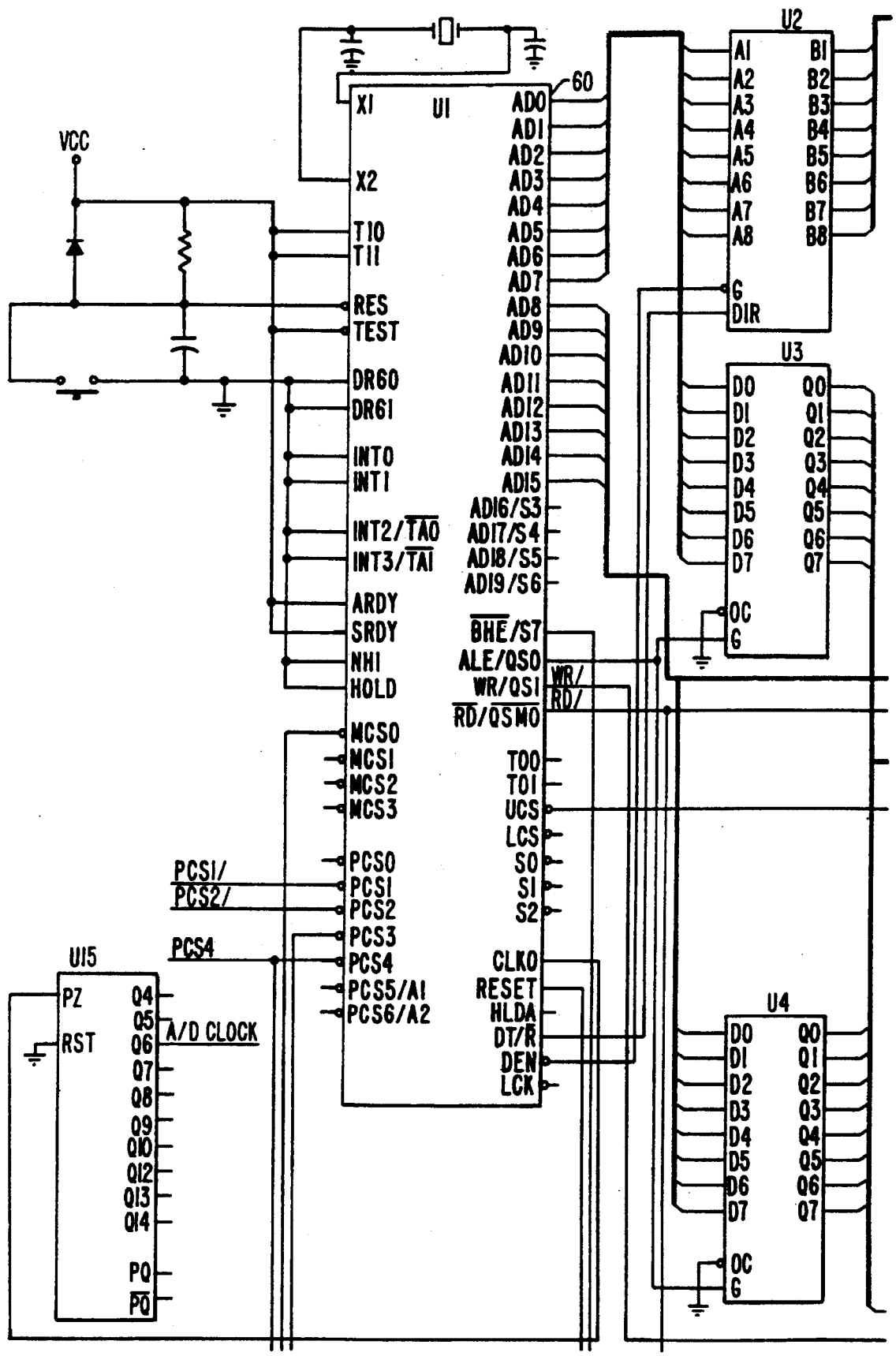
Figure 10B:
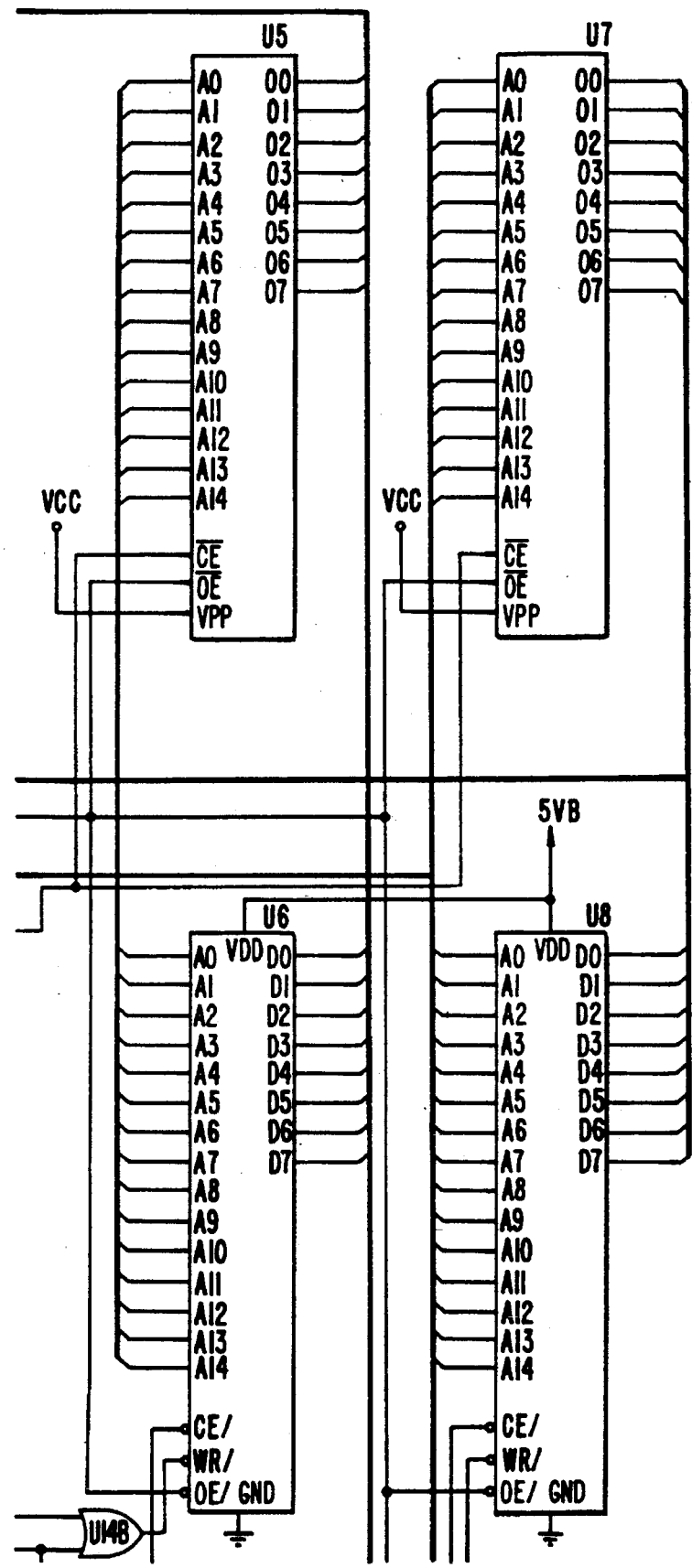
Figure 10C:
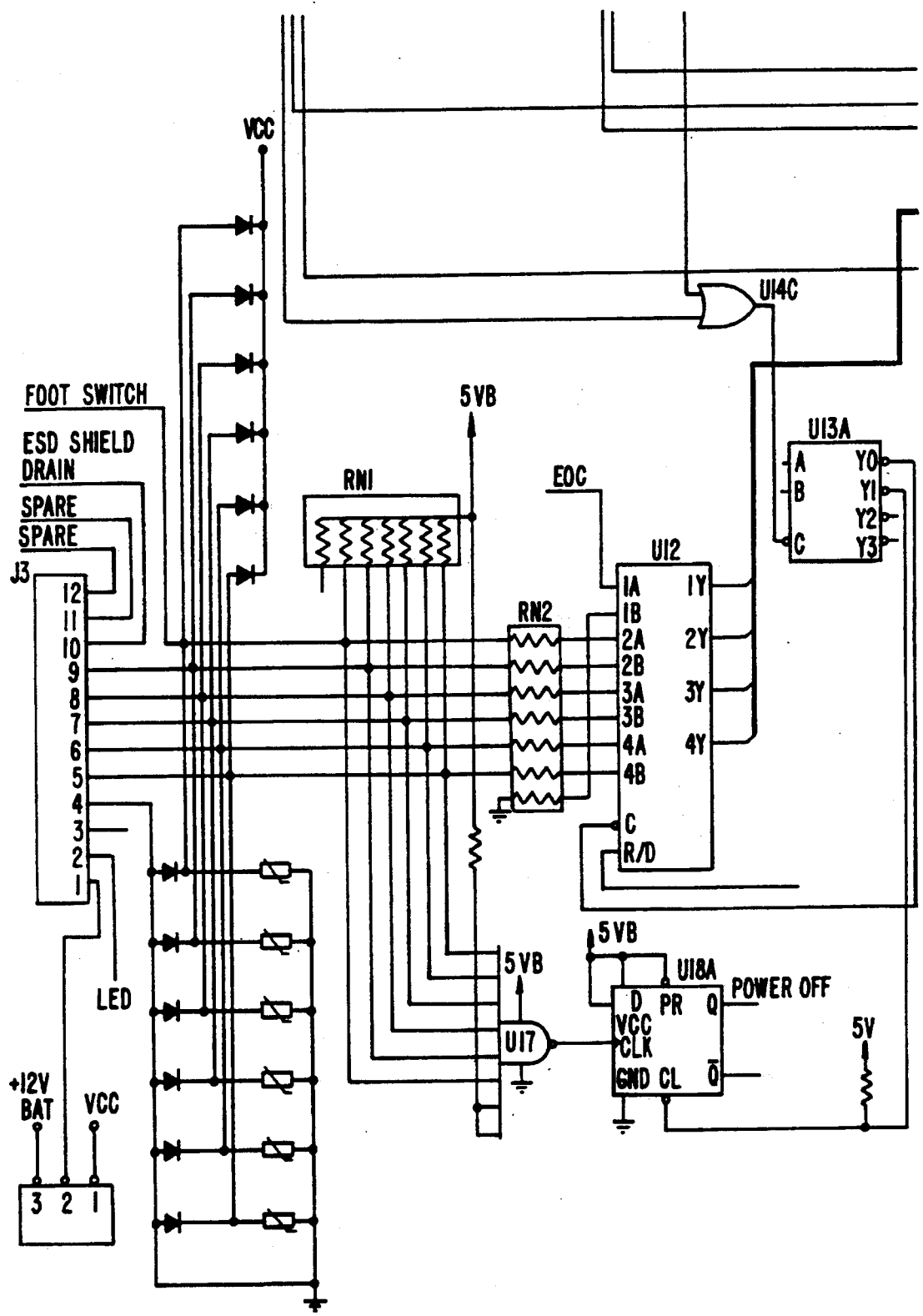
Figure 10D:
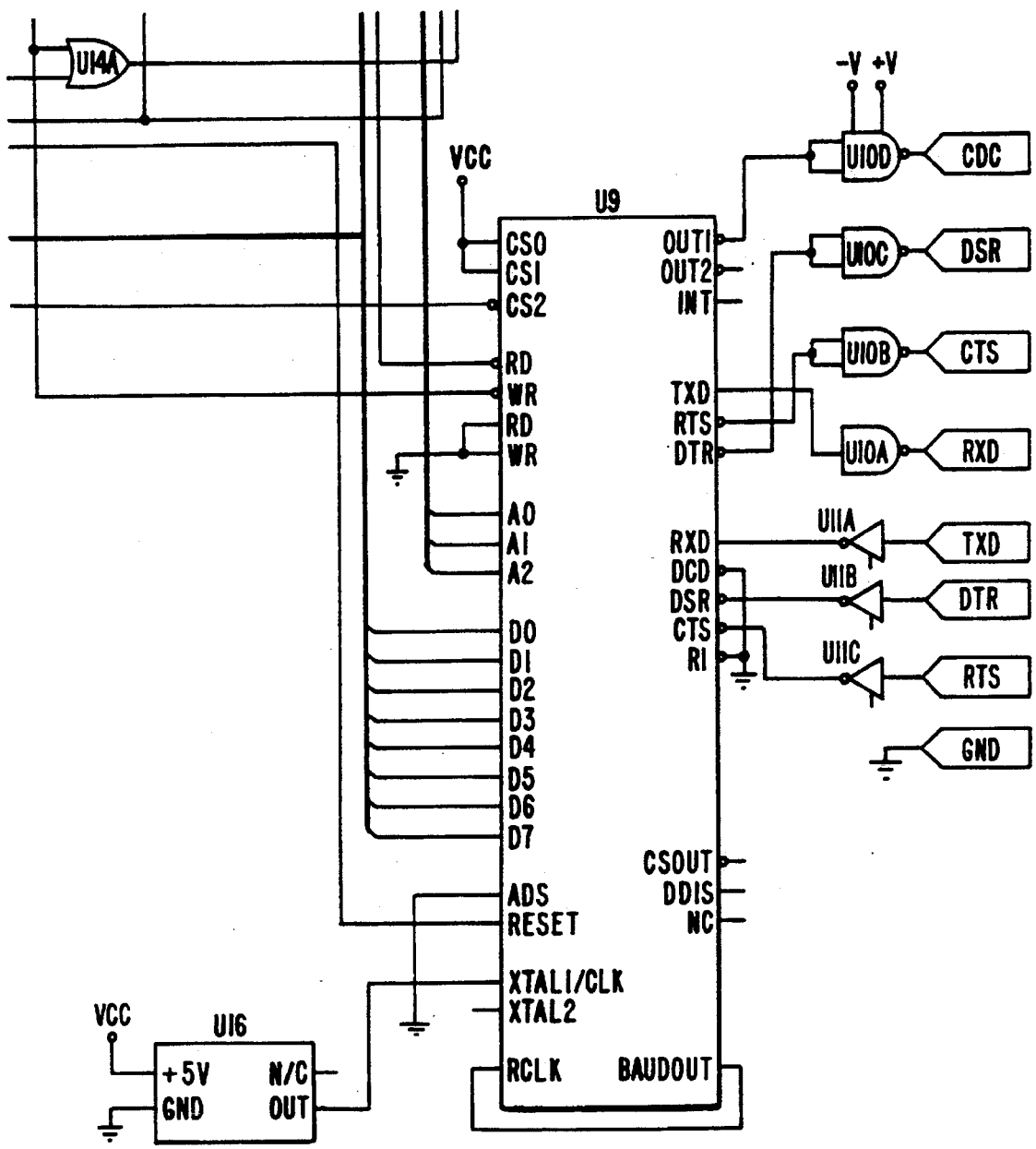
Figure 11A:
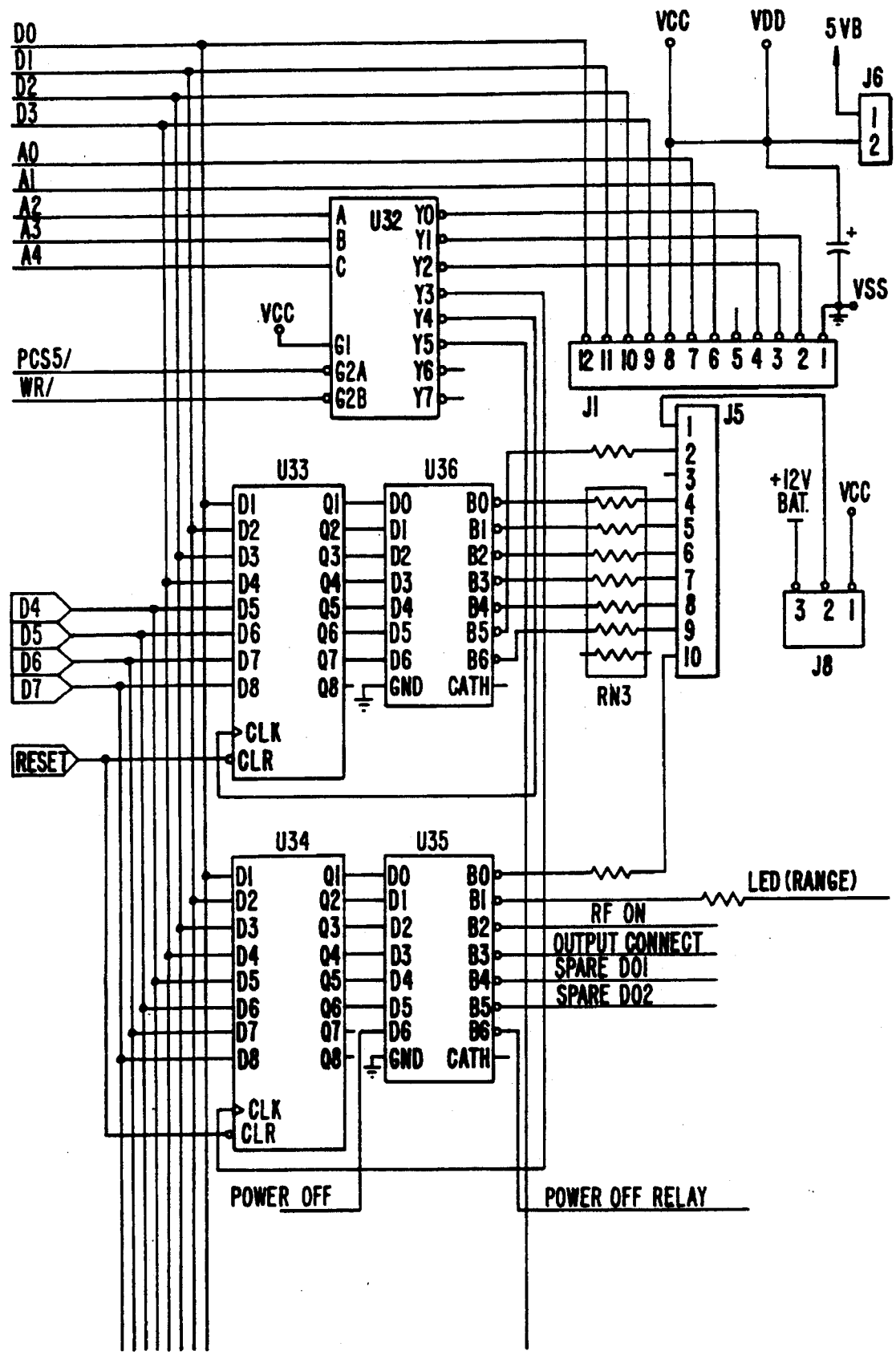
Figure 11B:
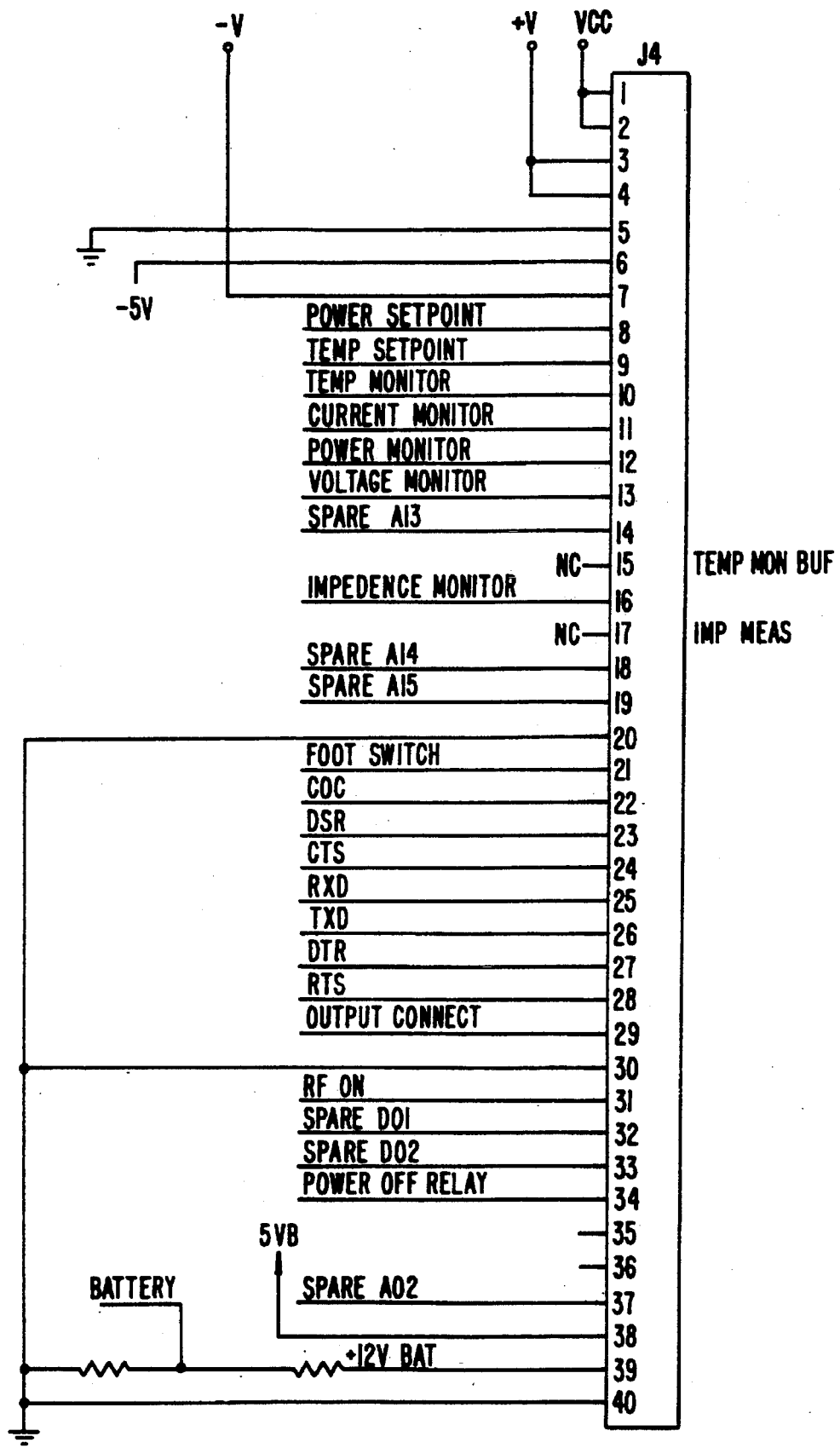
Figure 11C:
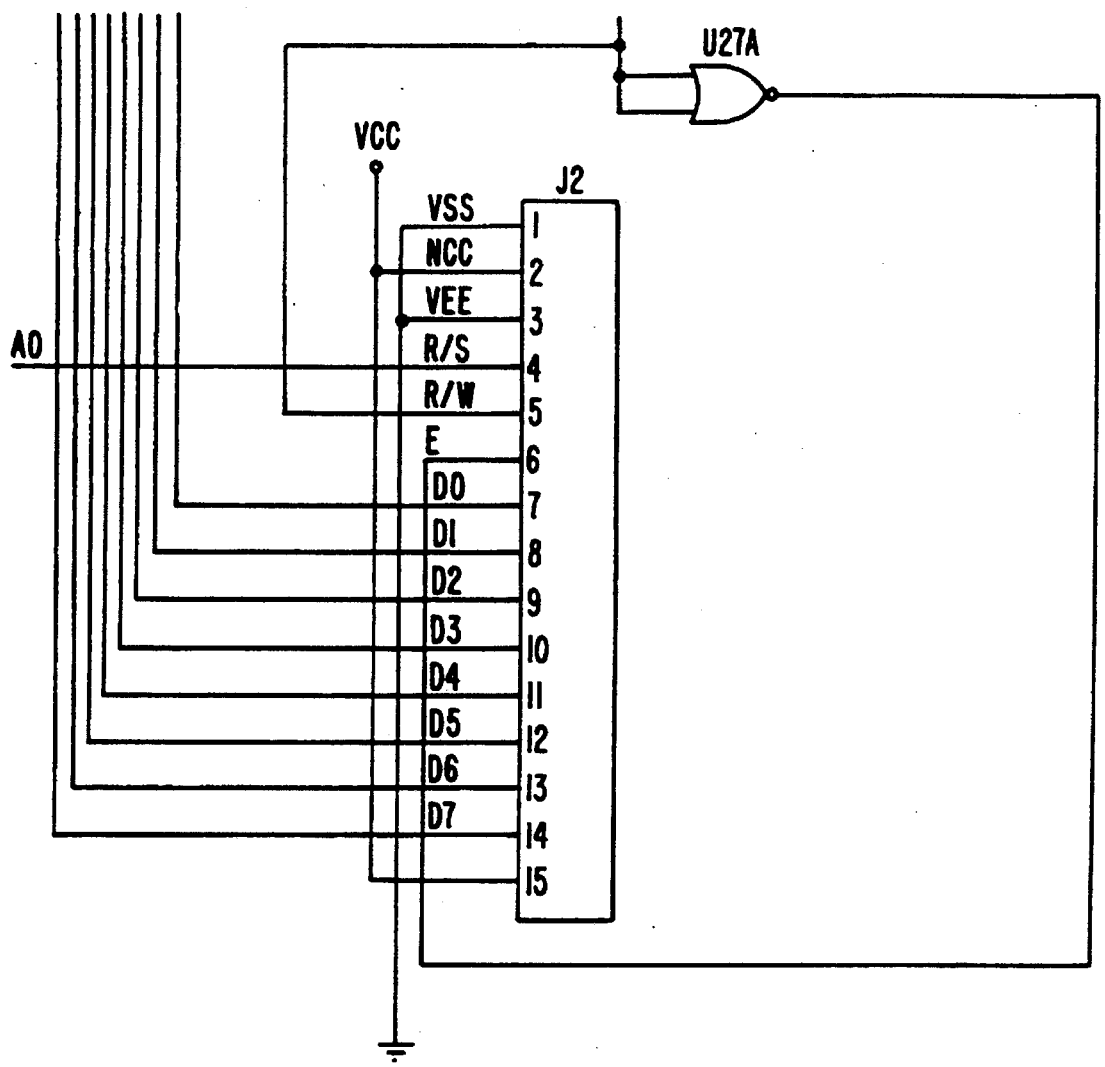
Figure 11:
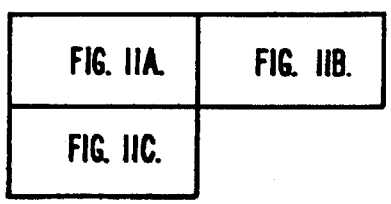

The microprocessor, operating via a 10 MHz clock, constantly monitors all function switches and zeros all DACs (inhibits any RF power command) in the event a malfunction is detected. The RF power generated by the unit cannot exceed 55 W. A comparator 94, shown in FIG. 7, shuts down RF power by limiting the duty cycle to final stage output transformer. Audible and visible alarms are provided in the following conditions: low battery; low/low battery prior to shut-down; low catheter impedance; high/low temperature; high power; and previously used catheter. The low impedance and a previously used catheter conditions inhibit any RF power command. In addition to the software controlled limits for temperature, power, and impedance (that turn off power if exceeded), there are also redundant hardware controls, including comparators 90, 96, that turn off power if the maximum temperature or power is exceeded.

Figure 6B:
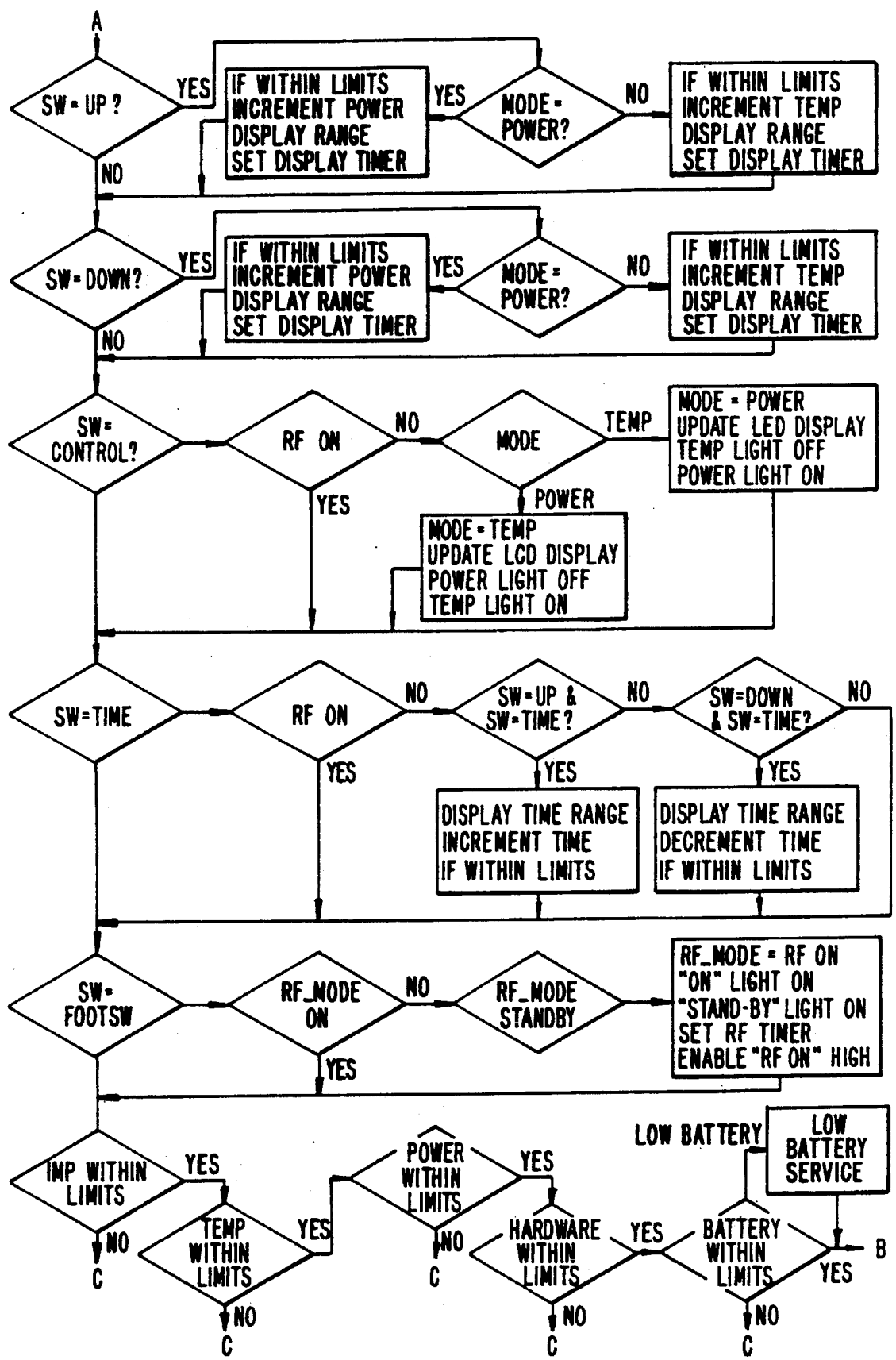

Use of the radiofrequency frequency ablation system 10 will begin by connecting the catheter 12 to the radiofrequency generator 18. After connection, the radiofrequency generator 18 will determine whether the fuse 34 is intact. This check-is performed by delivering a low current signal through lines 22c to the fuse 34. As shown in FIG. 12, fuse 34 is connected between a positive voltage source 98 and ground through optocouplers 100, 108, such that when the fuse is intact, current flows across the fuse and activates an optocoupler 100 which is connected to microprocessor 60 via connector 50. If fuse 34 is broken, optocoupler 100 remains deactivated so that a high voltage signal is sent from a positive voltage source 102 to the microprocessor. If the fuse is intact, optocoupler 100 is activated, connecting voltage source 102 through optocoupler to ground, resulting in a low voltage signal sent to microprocessor 60. The circuit shown in FIG. 12 thereby serves as a voltage sensor for sensing whether the fuse is intact. If current flow is detected, the fuse is noted to be intact and a second, higher current is applied to the fuse. Referring again to FIG. 12, a second optocoupler 104 is connected to the microprocessor via connector 50. The microprocessor sends a signal to optocoupler 104 to activate the optocoupler, which causes current flow from positive voltage source 106 to ground. This activates optocoupler 108, causing high current flow from voltage source 98 through optocoupler 108 through the fuse to ground, thus burning the fuse, if previously intact. The high current signal will blow the fuse so that the catheter is now "marked" as having been used. If the fuse is missing or burned, the generator will be disabled by sending a signal from microprocessor 60 through signal line 109 to a relay 110, shown in FIG. 7. Relay 110 decouples the power output 76 from connector 50, so as to decouple electrode connection wire 22a in the catheter (FIG. 1) from the power generator. System operation will continue generally as described above in connection with the system flow chart of FIG. 6.

After introducing the catheter to the desired location within the patient's heart, the user will select the desired power delivery mode, i.e. power control or temperature control mode. Of particular interest to the present invention, the temperature control mode utilizes the cascade temperature control scheme described previously. The user selects the desired temperature set point and power is applied with the radiofrequency generator 18 precisely controlling the amount of power delivered in order to maintain the electrode temperature at the set point. Verification of the result of the treatment may be made using the ECG components of the catheter 12, or may be made using other conventional diagnostic techniques. Treatment may be repeated one or more times in order to achieve the desired ablation of the accessory pathway or location on the bundle of HIS.

Although the foregoing invention has been described in some detail by way of illustration and example, for purposes of clarity of understanding, it will be obvious that certain changes and modifications may be practiced within the scope of the appended claims.

What is claimed is:

1. A system for radiofrequency ablation of cardiac tissue, said system comprising:

a catheter having a proximal end, a distal end, an electrode near said distal end, and a temperature sensor near said distal end, said electrode being coupled to an electrode connection wire extending to said proximal end, and said temperature sensor being coupled to a temperature sensor connection wire extending to said proximal end; and a radiofrequency power generator connectable to the proximal end of the catheter, said generator including:
 (a) a power source which delivers radiofrequency power to the electrode based on a power output signal;

(b) means for measuring radiofrequency power from the power source to produce an actual power signal;

(c) an analog temperature controller which receives a temperature set point signal and an actual temperature signal from the temperature sensor and based on a difference therebetween produces power set point signal;

(d) an analog power controller coupled to the means for measuring radiofrequency Dower and to the analog temperature controller, wherein the analog power controller receives the power set point signal and the actual power signal and based on a difference therebetween produces the power output signal; and means for connecting said power source to said electrode connection wire and for connecting said temperature controller to said temperature sensor connection wire.

2. A system as in claim 1, wherein the electrode is at the distal tip of the catheter.

3. A system as in claim 1, wherein the power source comprises a radiofrequency oscillator coupled to a power transformer.

4. A system as in claim 3, wherein the power transformer is coupled to the power controller to receive said power output signal.

5. A system as in claim 1, wherein the power set point signal is proportional to the difference between the actual temperature signal and the temperature set point signal.

6. A system as in claim 1, wherein the power output signal is proportional to the difference between the power set point signal and the actual power signal.

7. A system as in claim 1 further comprising means for optically isolating the temperature sensor from the radiofrequency power generator.

8. A system for radiofrequency ablation of tissue, said system comprising;

a catheter having a proximal end, a distal end, an electrode near said distal end, and a temperature sensor near said distal end, said electrode being coupled to an electrode connection wire extending to said proximal end, and said temperature sensor being coupled to a temperature sensor connection wire extending to said proximal end; and a radiofrequency power generator connectable to the proximal end of the catheter, said generator including:

(a) power supply means for delivering radiofrequency power to the electrode based on a power output signal:

(b) means for controlling temperature at the temperature sensor, said means being connected to receive an actual temperature signal from the sensor and to modulate the power output signal based on the difference between said actual temperature signal and a temperature set point, wherein the means for controlling temperature comprise an analog temperature control circuit which produces a power set point signal based on the difference between said actual temperature signal and the temperature set point and an analog power control circuit which modulates the power output signal based on a difference between the actual power output from the power source and the power set point signal; and (c) a battery connected to said power supply means and said means for controlling as the sole source of power for said radiofrequency power generator to reduce or eliminate spurious ground differential currents;

(d) means for connecting said power supply means to said electrode connection wire and for connecting said temperature control means to said temperature sensor connection wire.

9. A system for radiofrequency ablation of tissue, said system comprising:

a catheter having a proximal end, a distal end, an electrode near said distal end, and a temperature sensor near said distal end, said electrode being coupled to an electrode connection wire extending to said proximal end, and said temperature sensor being coupled to a temperature sensor connection wire extending to said proximal end; and a radiofrequency power generator connectable to the proximal end of the catheter, said generator including (a) power supply means for delivering radiofrequency power to the electrode based on a power output signal wherein the power output signal is proportional to the difference between the power set point signal and the actual power signal;

(b) means for controlling temperature at the temperature sensor, said means being connected to receive an actual temperature signal from the sensor and to modulate the power output signal based on the difference between said actual temperature signal and a temperature set point: and (c) a battery connected to said power supply means and said means for controlling as the sole source of power for said radiofrequency power generator to reduce or eliminate spurious around differential currents:

(d) means for connecting said power supply means to said electrode connection wire and for connecting said temperature control means to said temperature sensor connection wire.

10. A system for radiofrequency ablation, said system comprising:

a catheter having a proximal end including connecting means, a distal end, an electrode near the distal end, and a fuse, said electrode being coupled to an electrode connection wire extending to said proximal end and said fuse being coupled to first and second fuse connecting wires coupled to said connecting means;

a radiofrequency power generator connectable to the connecting means at the proximal end of the catheter for supplying radiofrequency power to said electrode through said electrode connection wire;

means in the generator coupled to said first and second fuse connecting wires, for (a) sensing the integrity of the fuse when the catheter is initially connected to the generator, (b) disabling operation of the generator if the fuse is initially broken, and (c) breaking the fuse if the fuse is initially intact, whereby the catheter cannot be reused; and means for connecting the radiofrequency power generator to the electrode connection wire and for connecting said sensing, disabling and breaking means to said fuse.

11. A system as in claim 10, wherein the electrode is at the distal tip of the catheter.

12. A system as in claim 10, wherein the means for sensing is a voltage sensor coupled to a microprocessor and coupled to said connecting means.

13. A system as in claim 10, wherein the means for disabling operation of the generator is a relay coupled to a microprocessor and coupled to said connecting means for electrically decoupling the electrode connection wire from the generator.

14. A system as in claim 10, wherein the means for breaking the fuse is a current source coupled to said connecting means and monitored by a microprocessor for applying a current to the fuse.

15. A system as in claim 10, wherein the fuse is disposed in the proximal end of the catheter and coupled between a pair of conductors for coupling to said connecting means.

16. A system for radiofrequency ablation of tissue, said system comprising:

a catheter having a proximal end, a distal end, an electrode near said distal end, and a temperature sensor near said distal end, said electrode being coupled to an electrode connection wire extending to said proximal end, and said temperature sensor being coupled to a temperature sensor connection wire extending to said proximal end;

a radiofrequency power generator connectable to the proximal end of the catheter, said generator including (a) a power source which delivers radiofrequency power to the electrode based on a power output signal;

(b) means for controlling temperature at the temperature sensor, said means being connected to receive a actual temperature signal from the sensor and to modulate the power output signal based on a control signal having a magnitude indicating the difference between said actual temperature signal and a temperature set point;

(c) means for connecting said power source to said electrode connection wire and for connecting said temperature control means to said temperature sensor connection wire; and (d) means for providing an alternative control signal having a magnitude indicating a selected power level;

(e) means, coupled to said means for providing said alternative control signal for limiting the radiofrequency power delivered to said electrode according to the magnitude of said alternative control signal and irrespective of said actual temperature signal or said temperature set point:

first means for disabling said operation of said radiofrequency power generator comprising a microprocessor coupled to said power source, said microprocessor controlled by software program programmed to disable said radiofrequency power generator based on a first parameter selected from the group including impedance of said electrode, radiofrequency power delivered to said electrode, and said actual temperature signal if at least one of said first parameters exceeds a first limit; and second means for disabling operation of said radiofrequency power generator based on a second parameter selected from the group including radiofrequency power delivered to said electrode and said actual temperature signal.

17. A system as in claim 16 wherein said second disabling means comprises at least one comparator coupled to the radiofrequency power source and the connecting means to disable said radiofrequency power source if at least one of said second parameters exceeds a second limit.

* * * * *